US012788851B2

(12) United States Patent
Gowans et al.

(10) Patent No.: US 12,788,851 B2
(45) **Date of Patent: *Nov. 10, 2026**

(54) POSITIONING OF SENSORS FOR SENSOR ENABLED WOUND MONITORING OR THERAPY

(71) Applicant: Smith & Nephew PLC, Watford (GB)

(72) Inventors: Philip Gowans, Rawcliffe (GB); Allan Kenneth Frazer Grugeon Hunt, Beverley (GB); Marcus Damian Phillips, Horbury (GB); Damian Smith, Swanland (GB); Charlotte Urwin, Hull (GB)

(73) Assignee: Smith & Nephew PLC, Watford (GB)

( * ) Notice: Subject to any disclaimer, the term of this patent is extended or adjusted under 35 U.S.C. 154(b) by 112 days.

This patent is subject to a terminal disclaimer.

(21) Appl. No.: 19/011,168

(22) Filed: Jan. 6, 2025

(65) Prior Publication Data

US 2025/0135076 A1 May 1, 2025

Related U.S. Application Data

(63) Continuation of application No. 18/581,326, filed on Feb. 19, 2024, now Pat. No. 12,214,111, which is a (Continued)

(51) Int. Cl.
*A61M 1/00* (2006.01)
*A61B 5/00* (2006.01)
(Continued)

(52) U.S. Cl.
CPC ............. *A61M 1/00* (2013.01); *A61B 5/0531* (2013.01); *A61B 5/14551* (2013.01);
(Continued)

(58) Field of Classification Search
CPC .......... A61M 1/00; A61M 1/73; A61M 1/915; A61M 1/916; A61M 1/95; A61M 1/982;
(Continued)

(56) References Cited

U.S. PATENT DOCUMENTS 8,925,392 B2 * 1/2015 Esposito .................. G01L 1/18 73/862.01
12,551,146 B2 2/2026 Ipsen et al.
(Continued)

*Primary Examiner* — Jonathan T Kuo
(74) *Attorney, Agent, or Firm* — Knobbe, Martens, Olson & Bear, LLP

(57) ABSTRACT

Embodiments of apparatuses and methods for determining a positioning of sensors in a wound dressing are disclosed. In some embodiments, a wound monitoring and/or therapy system can include a wound dressing and a plurality of sensors configured to measure one or more wound characteristics. The wound monitor system can also include at least one positioning device configured to indicate position and/or orientation in the wound of a sensor of the plurality of sensors. In some embodiments, a detector can be configured to determine, based on the positioning data, the position and/or orientation in the wound of the sensor of the plurality of sensors. In some embodiments, the plurality of sensors can be positioned on a strip or string of material in communication with the positioning device.

14 Claims, 36 Drawing Sheets

Related U.S. Application Data continuation of application No. 16/638,074, filed as application No. PCT/EP2018/071767 on Aug. 10, 2018, now Pat. No. 11,925,735.

(60) Provisional application No. 62/543,909, filed on Aug. 10, 2017.

(51) Int. Cl.

| | |
|---|---|
| ***A61B 5/0531*** | (2021.01) |
| ***A61B 5/1455*** | (2006.01) |
| ***A61F 13/84*** | (2006.01) |

(52) U.S. Cl.

CPC .............. *A61B 5/445* (2013.01); *A61F 13/84* (2013.01); *A61M 1/73* (2021.05); *A61M 1/915* (2021.05); *A61M 1/916* (2021.05); *A61M 1/95* (2021.05); *A61B 2560/0468* (2013.01); *A61B 2562/063* (2013.01); *A61B 2562/08* (2013.01); *A61F 2013/8473* (2013.01); *A61F 2013/8497* (2013.01); *A61M 1/982* (2021.05); *A61M 1/985* (2021.05)

(58) Field of Classification Search

CPC ..... A61M 2205/33; A61M 1/90–1/985; A61B 5/0531; A61B 5/14551; A61B 5/445; A61B 2560/0468; A61B 2562/063; A61B 2562/08; A61F 13/84; A61F 2013/8473; A61F 2013/8497; A61F 13/05

See application file for complete search history.

(56) References Cited

U.S. PATENT DOCUMENTS

| | | | | |
|---|---|---|---|---|
| 2009/0209896 | A1 | 8/2009 | Selevan | |
| 2012/0116485 | A1 | 5/2012 | Burgmann | |
| 2013/0133822 | A1 | 5/2013 | Koetse et al. | |
| 2013/0192071 | A1 * | 8/2013 | Esposito ................ | A43B 17/00 324/693 |
| 2014/0062462 | A1 | 3/2014 | McChrystal et al. | |
| 2015/0177080 | A1 * | 6/2015 | Esposito .................. | A61B 5/01 73/862.01 |

* cited by examiner

POSITIONING OF SENSORS FOR SENSOR ENABLED WOUND MONITORING OR THERAPY

RELATED APPLICATIONS

This application is a continuation of U.S. application Ser. No. 18/581,326, filed Feb. 19, 2024, which is a continuation of U.S. application Ser. No. 16/638,074, filed Feb. 10, 2020, which is a U.S. national stage application of International Patent Application No. PCT/EP2018/071767, filed Aug. 10, 2018, which claims priority to U.S. Provisional Patent Application No. 62/543,909, filed on Aug. 10, 2017, which is hereby incorporated by reference in its entirety and made part of this disclosure.

FIELD

Embodiments of the present disclosure relate to apparatuses, systems, and methods for the treatment of tissues via sensor-enabled monitoring in communication with various therapy regimes.

BACKGROUND

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

SUMMARY

Embodiments of the present disclosure relate to apparatuses and methods for wound treatment. Some of the wound treatment apparatuses described herein comprise a negative pressure source or a pump assembly or system for providing negative pressure to a wound. Wound treatment apparatuses may also comprise wound dressings that may be used in combination with the negative pressure sources and pump assemblies described herein.

In some aspects, a wound monitoring and/or therapy system can comprise a wound dressing configured to be positioned in contact with a wound, the wound dressing can comprise a plurality of sensors configured to measure one or more wound characteristics, wherein the plurality of sensors are arranged on a sensor strip or a string of sensors, at least one positioning device configured to indicate position and/or orientation in the wound of a first sensor of the plurality of sensors and a detector configured to determine, based on the positioning data, the position and/or orientation in the wound of the first sensor of the plurality of sensors.

The system of the preceding paragraph may also include any combination of the following features described in this paragraph, among others described herein. In some embodiments, the plurality of sensors can include at least one nanosensor, thermistor, conductivity sensor, Sp02 sensor, pH sensor, color sensor, optical sensor, impedance sensor, or electrode. In some embodiments, the optical sensor can comprise at least one of a red, green, blue, and clear (RGBC) sensor or red, green blue, and white (RGBW) sensor. In some embodiments, the plurality of sensors can be arranged on a sensor strip. In some embodiments, the at least one positioning device can be attached to or integrated within the sensor strip. In some embodiments, the plurality of sensors can be arranged on a string of sensors. In some embodiments, the at least one positioning device can be configured to wirelessly communicate with the string of sensors. In some embodiments, the at least one positioning device can be configured to electrically communicate with the string of sensors. In some embodiments, the detector can comprise a controller configured to determine the position and/or orientation in the wound of the first sensor of the plurality of sensors based at least on the received positioning data and a relationship between positions and/or orientations in the wound dressing and/or the wound of the at least one positioning device and first sensor. In some embodiments, the relationship can comprise at least known position and/or orientation offset between positioning and first sensors. In some embodiments, the portion of the at least one positioning device can be positioned outside of the wound. In some embodiments, the at least one positioning device can comprise at least one marking configured to communicate positioning information. In some embodiments, the at least one marking can comprise at least one of a barcode, a number, a letter, an alphanumeric code, a standard shape, an irregular shape, or a logo. In some embodiments, the wound dressing can be configured to communicate negative pressure to the wound. In some embodiments, a kit comprising the wound dressing described herein and a negative pressure source configured to be fluidically connected to the wound dressing.

In some aspects, a method of operating a wound monitoring and/or therapy system. The method can comprise a wound dressing including a plurality of sensors arranged on a sensor strip or a string of sensors configured to measure one or more wound characteristics, the method comprising collecting, from a positioning device positioned in or on the wound dressing, positioning data with a detector positioned over the wound dressing when the wound dressing is positioned over the wound and determining, with a controller, position and/or orientation in the wound of a first sensor from the plurality of sensors based on the positioning data.

The method of the preceding paragraph may also include any combination of the following features described in this paragraph, among others described herein. In some embodiments, the plurality of sensors can include at least one nanosensor, thermistor, conductivity sensor, Sp02 sensor, pH sensor, color sensor, optical sensor, impedance sensor, or electrode. In some embodiments, the optical sensor can comprise at least one of a red, green, blue, and clear (RGBC) sensor or red, green blue, and white (RGBW) sensor. In some embodiments, the plurality of sensors can be arranged on a sensor strip. In some embodiments, the positioning device can be attached to or integrated within the sensor strip. In some embodiments, the plurality of sensors can be arranged on a string of sensors. In some embodiments, the positioning device can be in wireless communication with the string of sensors. In some embodiments, the positioning device can comprise an optical sensor configured to receive information wirelessly from one or more light sources on, in, or near the wound. In some embodiments, the positioning device can be in electrical communication with the string of sensors. In some embodiments, the method can further comprise determining, by the controller, a position and/or orientation in the wound of a second sensor of the plurality of sensors based at least on the received positioning data and a relationship between positions and/or orientations in the wound dressing and/or the wound of the positioning device and the first and second sensors. In some embodiments, the method can further comprising communicating negative pressure to the wound.

In some aspects, a wound monitoring and/or therapy system, can comprise a wound dressing configured to be positioned in contact with a wound, a sensor tag, strip, or string comprising a plurality of sensors configured to measure one or more wound characteristics, and wherein the sensor tag, strip, or string is configured to be positioned in at least one of the wound or an area surrounding the wound.

The system of the preceding paragraph may also include any combination of the following features described in this paragraph, among others described herein. In some embodiments, the plurality of sensors can include at least one nanosensor, thermistor, conductivity sensor, Sp02 sensor, pH sensor, color sensor, optical sensor, impedance sensor, or electrode. In some embodiments, the optical sensor can comprise at least one of a red, green, blue, and clear (RGBC) sensor or red, green blue, and white (RGBW) sensor. In some embodiments, the sensor strip or tag can comprise a portion of the sensor strip or tag configured to be positioned at the area surrounding the wound. In some embodiments, the sensor strip or tag can comprise a portion of the sensor strip or tag configured to be positioned in the wound. In some embodiments, the portion of the sensor strip or tag configured to be positioned in the wound can be configured to be positioned at an edge of the wound. In some embodiments, the portion of the sensor strip or tag configured to be positioned in the wound can be configured to be positioned at a center portion of the wound. In some embodiments, the sensor strip or tag can comprise a portion of the sensor strip or tag configured to be positioned at the area surrounding the wound and a portion of the sensor strip or tag is configured to be positioned in the wound. In some embodiments, the sensor string can be configured to be positioned in the wound. In some embodiments, the sensor string, sensor strip, and sensor tag can be configured to be in communication with a component configured to be positioned at the area surrounding the wound or remote from the wound. In some embodiments, the wound dressing can be configured to communicate negative pressure to the wound. In some embodiments, a kit comprising the wound dressing and a negative pressure source can be configured to be fluidically connected to the wound dressing.

In some aspects, a wound monitoring and/or therapy system can comprise a wound dressing configured to be positioned in contact with a wound. The wound dressing can comprise a sensor support material comprising a plurality of sensors configured to measure one or more wound characteristics, wherein the plurality of sensors are configured to be positioned in at least one of the wound or an area surrounding the wound, the sensor support material comprising a plurality of tracks positioned on the sensor support material, wherein the sensor support material comprises a plurality of slits positioned between at least two adjacent tracks, positioned between at least two adjacent sensors, or positioned between at least one track and at least one adjacent sensor.

The system of the preceding paragraph may also include any combination of the following features described in this paragraph, among others described herein. In some embodiments, the sensor support material can comprise a sensor tag, strip, or string comprising at least one sensor of the plurality of sensors. In some embodiments, a slit of the plurality of slits can substantially surround a perimeter of a sensor of the plurality of sensors. In some embodiments, the plurality of sensors can include at least one nanosensor, thermistor, conductivity sensor, Sp02 sensor, pH sensor, color sensor, optical sensor, impedance sensor, or electrode. In some embodiments, the optical sensor can comprise at least one of a red, green, blue, and clear (RGBC) sensor or red, green blue, and white (RGBW) sensor. In some embodiments, the sensor strip or tag can comprise a portion of the sensor strip or tag configured to be positioned at the area surrounding the wound. In some embodiments, the sensor strip or tag can comprise a portion of the sensor strip or tag configured to be positioned in the wound. In some embodiments, the portion of the sensor strip or tag configured to be positioned in the wound can be configured to be positioned at an edge of the wound. In some embodiments, the portion of the sensor strip or tag configured to be positioned in the wound can be configured to be positioned at a center portion of the wound. In some embodiments, the sensor strip or tag can comprise a portion of the sensor strip or tag configured to be positioned at the area surrounding the wound and a portion of the sensor strip or tag is configured to be positioned in the wound. In some embodiments, the sensor string can be configured to be positioned in the wound. In some embodiments, the sensor string, sensor strip, and sensor tag can be configured to be in communication with a component configured to be positioned at the area surrounding the wound or remote from the wound. In some embodiments, the wound dressing can be configured to communicate negative pressure to the wound. In some embodiments, a kit comprising the wound dressing and a negative pressure source can be configured to be fluidically connected to the wound dressing. In some embodiments, a method of manufacturing the wound dressing can comprise laser cutting the plurality of slits in the sensor support material.

Any of the features, components, or details of any of the arrangements or embodiments disclosed in this application, including without limitation any of the wound dressing embodiments, pump embodiments, and any of the negative pressure wound therapy embodiments disclosed below, are interchangeably combinable with any other features, components, or details of any of the arrangements or embodiments disclosed herein to form new arrangements and embodiments.

DETAILED DESCRIPTION

Figure 1A:
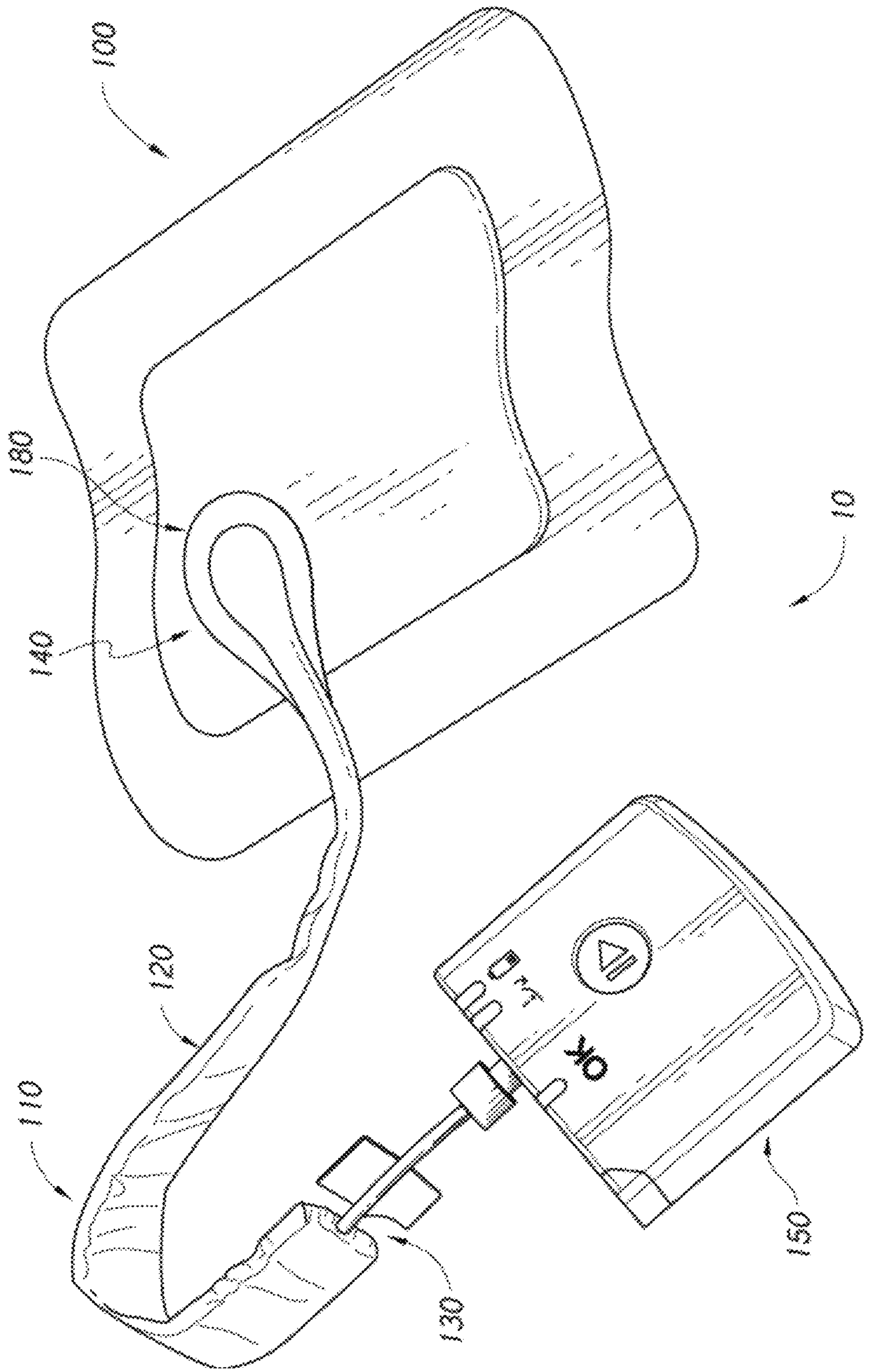
FIG. 1A illustrates a negative pressure wound treatment system employing a flexible fluidic connector and a wound dressing capable of absorbing and storing wound exudate according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

- an absorbent layer for absorbing wound exudate and
- an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film. Typically, the translucent film has a moisture vapour permeability of 500 g/m2/24 hours or more.

The translucent film may be a bacterial barrier.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 μm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

NPWT System Overview

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

However, prior art dressings for use in negative pressure wound therapy or other wound therapy provide little visualization or information of the condition of the wound beneath the dressing. This can require the dressing to be changed prematurely before the desired level of wound healing has occurred or, for absorbent dressings, prior to the full absorbent capacity of the dressing being reached to allow the clinician to inspect the healing and status of the wound. Some current dressings have limited and/or unsatisfactory methods or features of providing information of conditions of the wound.

Embodiments disclosed herein relate to apparatuses and methods of treating a wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning and the examples and description previously described, includes any body part of a patient that may be treated, such as by using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in International Application PCT/EP2016/059329 filed Apr. 26, 2016, entitled "REDUCED PRESSURE APPARATUS AND METHODS".

Figure 1B:
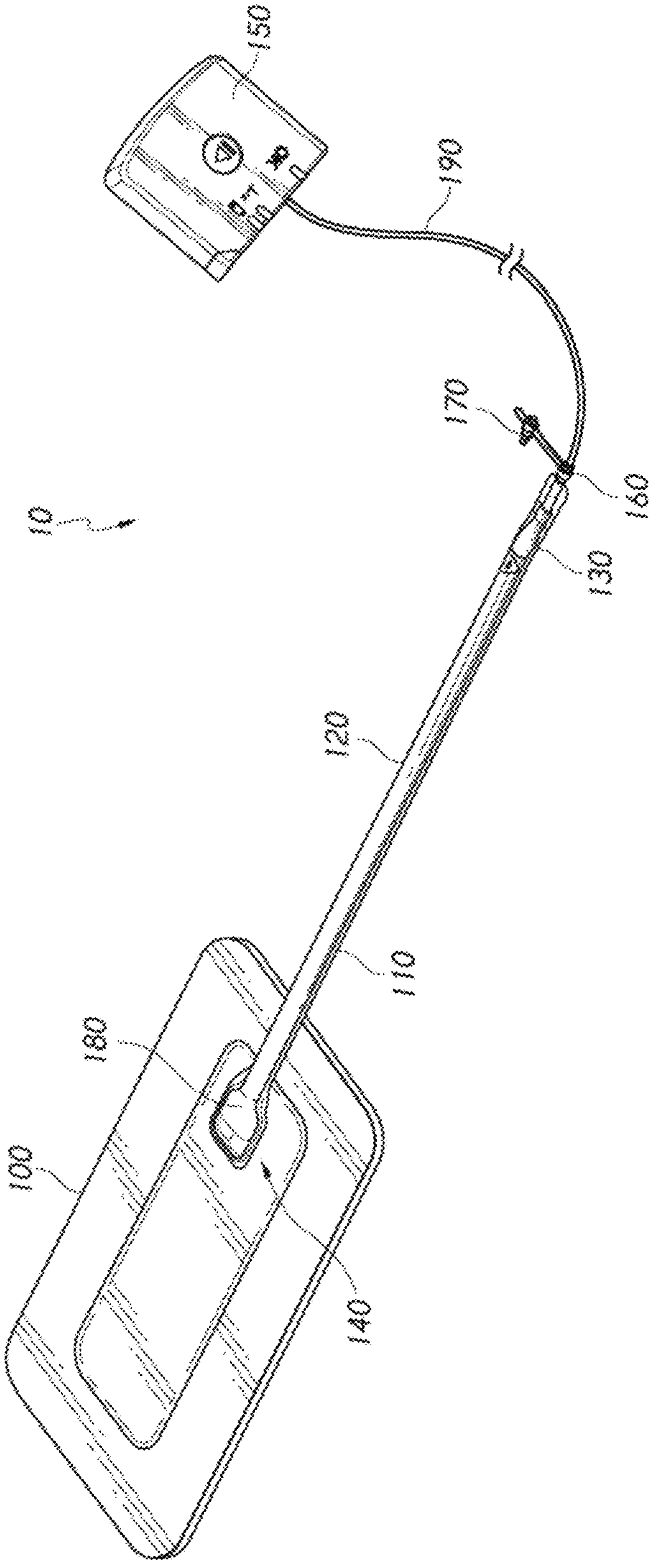
FIG. 1B illustrates a negative pressure wound treatment system employing a flexible fluidic connector and a wound dressing capable of absorbing and storing wound exudate according to some embodiments.

FIGS. 1A-B illustrate embodiments of a negative pressure wound treatment system 10 employing a wound dressing 100 in conjunction with a fluidic connector 110. Here, the fluidic connector 110 may comprise an elongate conduit, for example, a bridge 120 having a proximal end 130 and a distal end 140, and an applicator 180 at the distal end 140 of the bridge 120. An optional coupling 160 can be disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Wound Dressing Overview

Figure 2A:
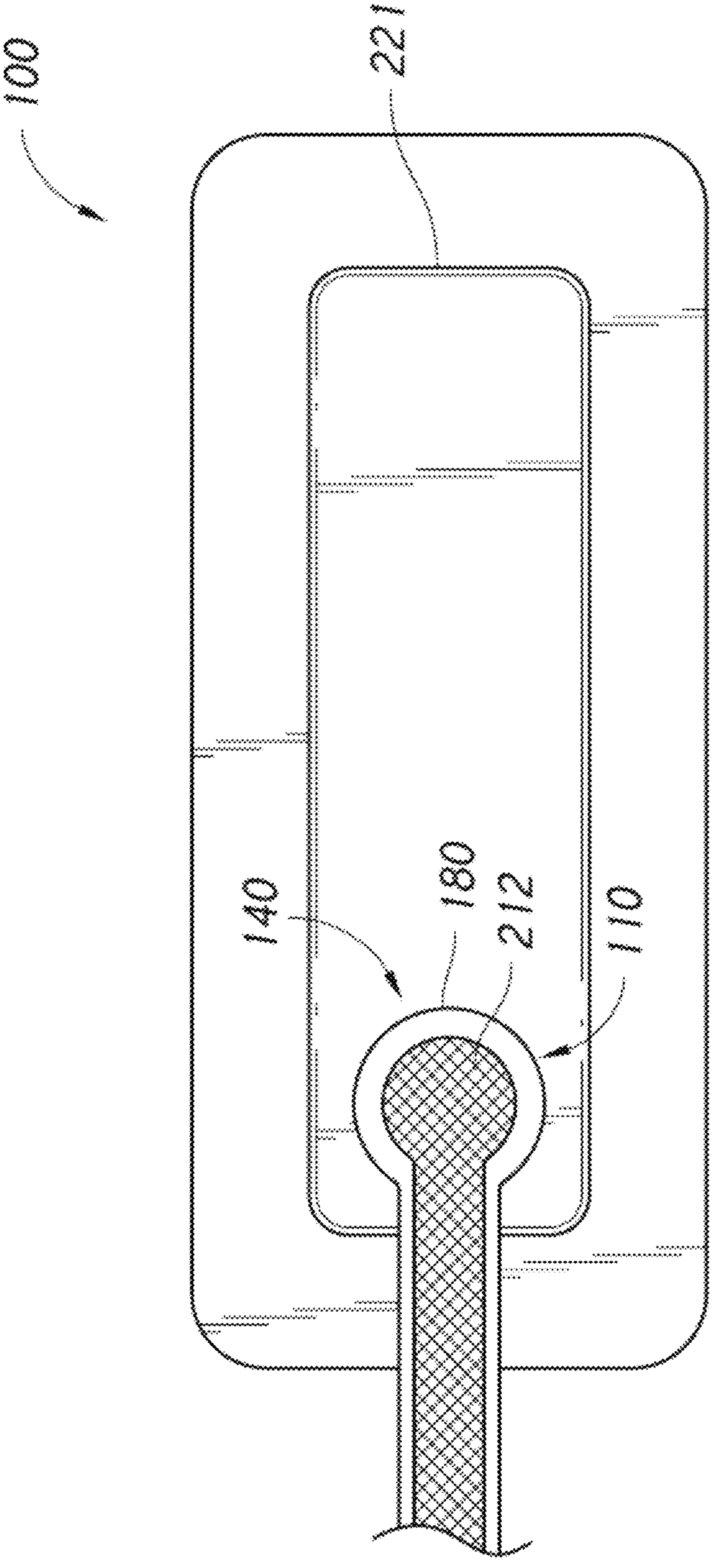
FIG. 2A illustrates a negative pressure wound treatment system employing a flexible fluidic connector and a wound dressing capable of absorbing and storing wound exudate according to some embodiments.

As shown in FIG. 2A, the fluidic connector 110 can comprise an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In an embodiment, the head 140 may measure 30 mm along its widest edge. The head 140 forms at least in part the applicator 180, described above, that is configured to seal against a top surface of the wound dressing.

Figure 2B:
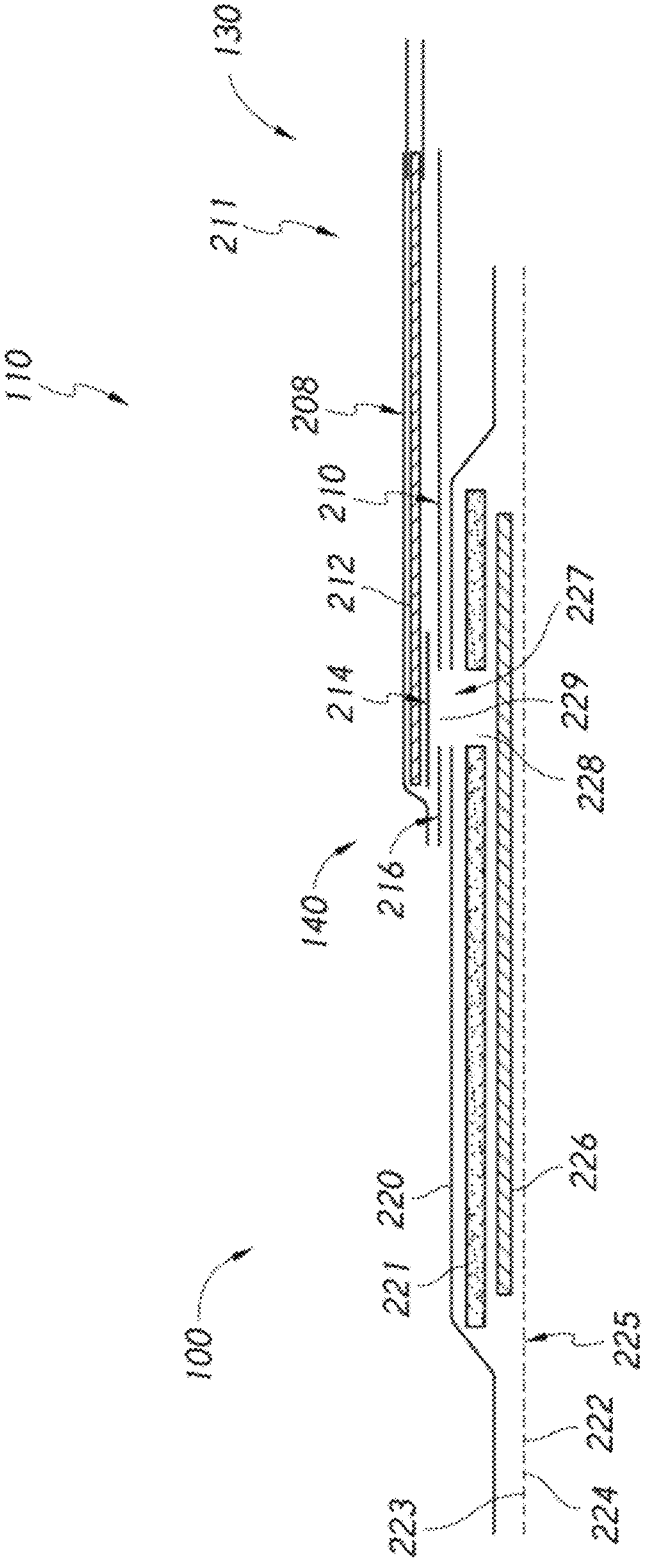
FIG. 2B illustrates a cross section of a fluidic connector connected to a wound dressing according to some embodiments.

FIG. 2B illustrates a cross-section through a wound dressing 100 similar to the wound dressing 10 as shown in FIG. 1B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located in or over a wound to be treated. The dressing 100 may be placed as to form a sealed cavity over the wound. In an embodiment, the dressing 100 comprises a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 can comprise through holes in the wound contact layer 222 which enable fluid to flow through the layer 222. The wound contact layer 222 helps prevent tissue ingrowth into the other material of the wound dressing. The perforations can be small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

To improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound. In some embodiments, the layer 10 may also aid in drawing fluids towards the backing layer 220.

The material of the absorbent layer 221 may also prevent liquid collected in the wound dressing 100 from flowing freely within the dressing, and can act so as to contain any liquid collected within the dressing. The absorbent layer 221 also helps distribute fluid throughout the layer via a wicking action so that fluid is drawn from the wound and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising superabsorbent powder, fibrous material such as cellulose, and bonding fibers. In an embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 100. The fluidic connector 110 can be attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

The absorbent layer 221 can include at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 can be gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can comprise two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, the fluidic connector 110 and through hole can be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound.

Turning now to the fluidic connector 110, some embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. Pat. No. 8,801,685, which is incorporated by reference herein in its entirety.

The fluid passage 212 can be constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure and/or vented air to the wound, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric.

In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

The filter element 214 can be impermeable to liquids, but permeable to gases, and is provided to act as a liquid barrier and to ensure that no liquids are able to escape from the wound dressing 100. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. The wound dressing 100 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 2C:
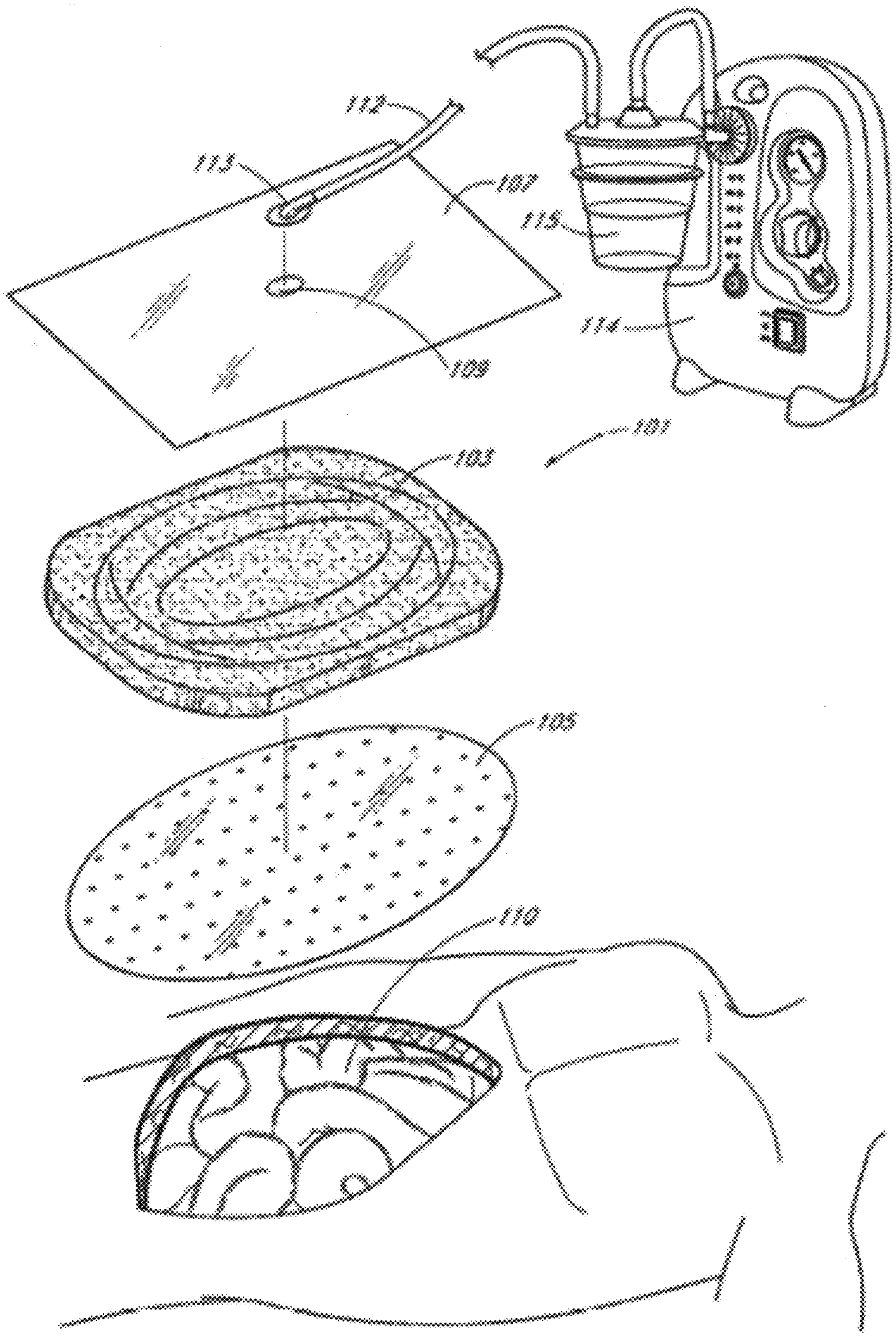
FIG. 2C illustrates of a negative pressure wound therapy system according to some embodiments.

Turning to FIG. 2C, treatment of other wound types, such as larger abdominal wounds, with negative pressure in certain embodiments uses a negative pressure treatment system 101 as illustrated schematically here. In this embodiment, a wound 106, illustrated here as an abdominal wound, may benefit from treatment with negative pressure. Such abdominal wounds may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening-particularly in the abdominal cavity-remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound. The application of reduced or negative pressure to a wound has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound 106 can be beneficial to a patient.

Accordingly, certain embodiments provide for a wound contact layer 105 to be placed over the wound 106. The wound contact layer can also be referred to as an organ protection layer and/or a tissue protection layer. The wound contact layer 105 can be a thin, flexible material which will not adhere to the wound or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound 106 or the transmittal of negative pressure to the wound 106. Additional embodiments of the wound contact layer 105 are described in further detail below.

Certain embodiments of the negative pressure treatment system 101 may also use a porous wound filler 103, which can be disposed over the wound contact layer 105. This pad 103 can be constructed from a porous material, for example foam, that is soft, resiliently flexible, and generally conformable to the wound 106. Such a foam can include an open-celled and reticulated foam made, for example, of a polymer. Suitable foams include foams composed of, for example, polyurethane, silicone, and polyvinyl alcohol. This pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other embodiments of wound fillers that may be used in place of or in addition to the pad 103 are discussed in further detail below.

A drape 107 can be used to seal the wound 106. The drape 107 can be at least partially liquid impermeable, such that at least a partial negative pressure may be maintained at the wound. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or olcophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be desirable to provide an odor filter, such as an activated charcoal canister.

Figure 2D:
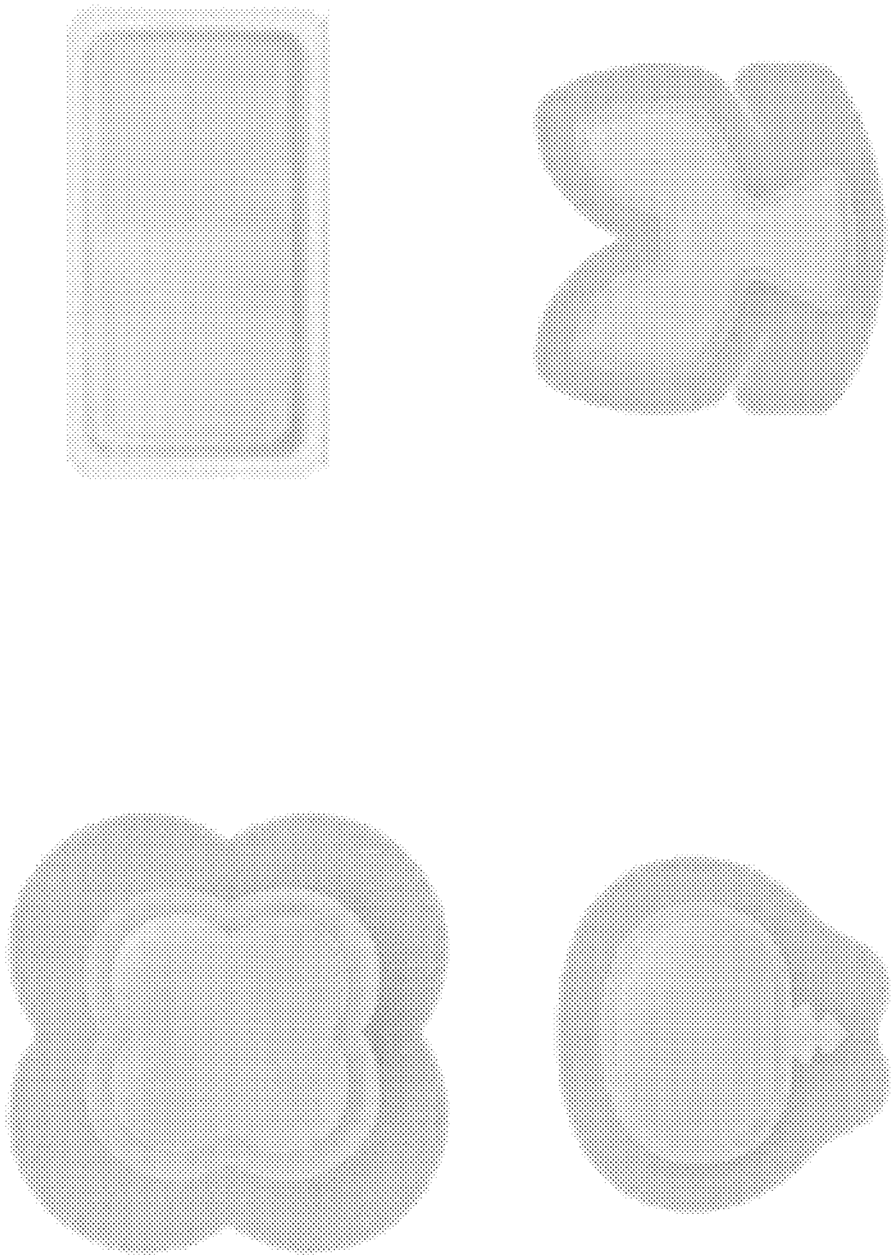
FIG. 2D illustrates a wound treatment system employing a wound dressing capable of absorbing and storing wound exudate to be used without negative pressure according to some embodiments.

FIG. 2D illustrates various embodiments of wound dressings that can be used for healing a wound without negative pressure. As shown in the dressings of FIG. 2D, the wound dressings can have multiple layers similar to the dressings described with reference to FIGS. 1A-1B and 2A-2B except the dressings of FIG. 2D do not include a port or fluidic connector. The wound dressings of FIG. 2D can include a cover layer and wound contact layer as described herein. The wound dressing can include various layers positioned between the wound contact layer and cover layer. For example, the dressing can include one or more absorbent layers and/or one or more transmission layers as described herein with reference to FIGS. 1A-1B and 2A-2B. Additionally, some embodiments related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to embodiments of wound dressings, the wound dressing components and principles, and the materials used for the wound dressings.

Wound Dressing with Sensors

A wound dressing that incorporates a number of sensors can be utilized in order to monitor characteristics of a wound as it heals, provide therapy to the wound, monitor patient movement, etc. Collecting data from the wounds that heal well, and from those that do not, can provide useful insights towards identifying measurands to indicate whether a wound is on a healing trajectory. International Patent Application No. PCT/IB2017/000693, filed May 5, 2017 titled "SENSOR ENABLED NEGATIVE PRESSURE WOUND THERAPY APPARATUS," is incorporated by reference in its entirety. International Patent Application No. PCT/IB2017/000693 describes various example embodiments and features related to apparatuses, systems, and methods the treatment of wounds, for example using dressings in combination with negative pressure wound therapy. The embodiments described herein are compatible with and can be part of the embodiments described in International Patent Application No. PCT/IB2017/000693, and some or all of the features described herein can be used or otherwise combined together or with any of the features described in International Patent Application No. PCT/IB2017/000693.

Figure 3A:
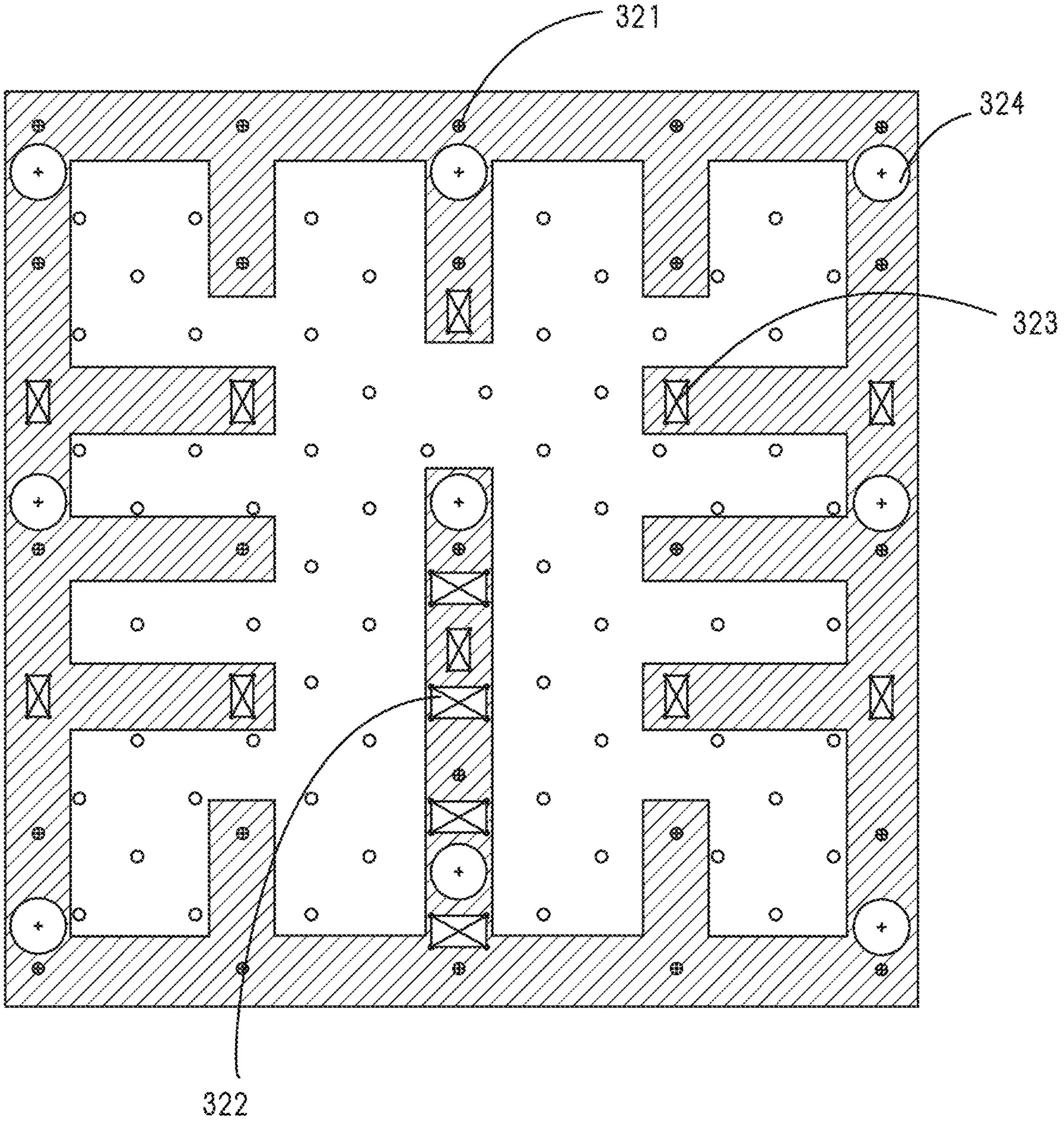
FIG. 3A illustrates a sensor array illustrating the sensor placement incorporated into a wound dressing component according to some embodiments.
Figure 3B:
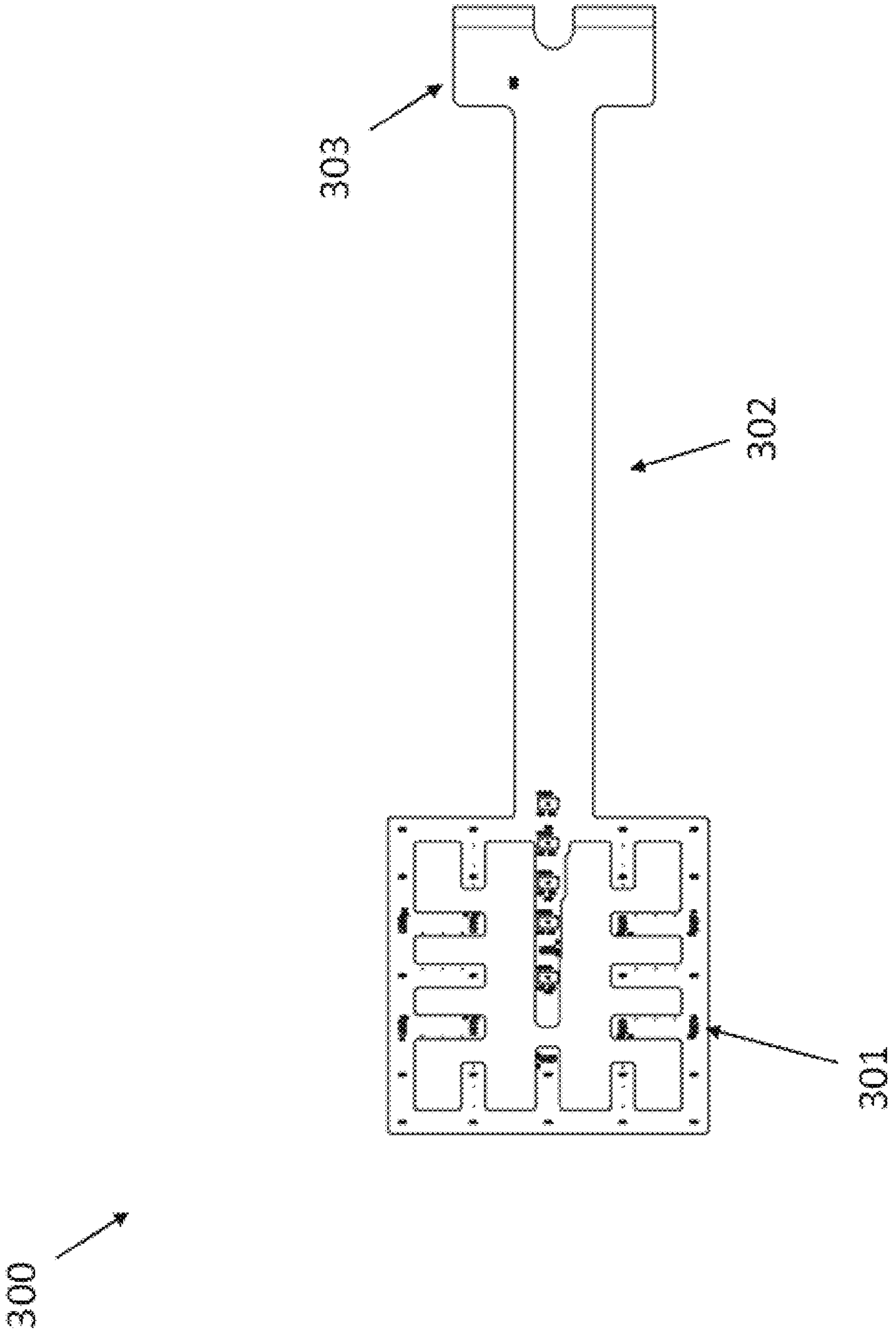
FIG. 3B illustrates a flexible sensor array including a sensor array portion, a tail portion, and a connector pad end portion according to some embodiments.
Figure 3F:
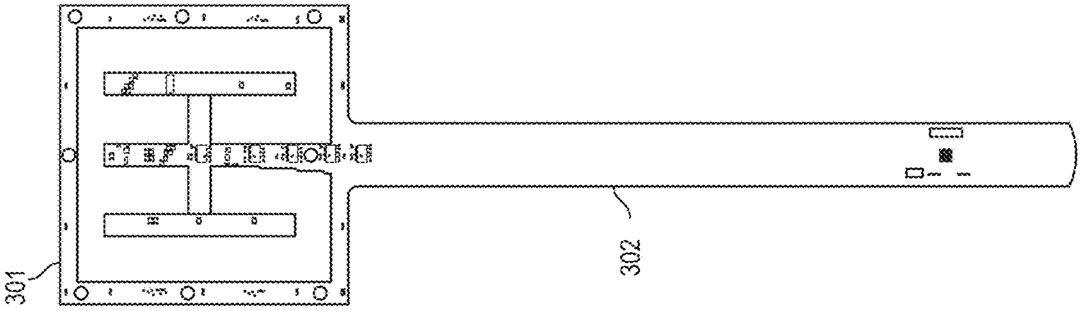
FIGS. 3C-3F show embodiments of the flexible circuit boards with four different sensor array geometries.
Figure 3E:
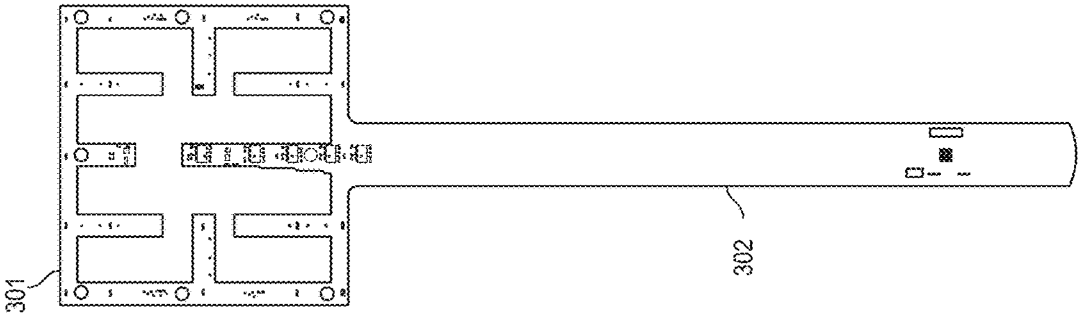

A number of sensor technologies can be used in wound dressings or one or more components forming part of an overall wound dressing apparatus. For example, as illustrated in FIGS. 3A and 3H, sub-sets of sensors can be incorporated onto or into a wound contact layer, which may be a perforated wound contact layer as shown in FIG. 3H. The wound contact layer in FIGS. 3A and 3H is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing apparatus and/or components of a wound dressing apparatus similar to those described with reference to FIG. 2C (e.g., gauze, foam or other wound packing material, a superabsorbent layer, a drape, a fully integrated dressing like the Pico or Allevyn Life dressing, etc.). In other embodiments, the sensor integrated wound contact layer may be part of a single unit dressing such as described in FIGS. 1A-2B and 2D.

The sensor integrated wound contact layer can be placed in contact with the wound and will allow fluid to pass through the contact layer while causing little to no damage to the tissue in the wound. The sensor integrated wound contact layer can be made of a flexible material such as silicone and can incorporate antimicrobials and/or other therapeutic agents known in the art. In some embodiments, the sensor integrated wound contact layer can incorporate adhesives that adhere to wet or dry tissue. In some embodiments, the sensors and/or sensor array can be incorporated into or encapsulated within other components of the wound dressing such as the absorbent layer and/or spacer layer described above.

As shown in FIGS. 3A and 3H, a sub-set of five sensors can be used including sensors for temperature (e.g., 25 thermistor sensors, in a 5×5 array, ~20 mm pitch), SpO2 (e.g., 4 or 5 SpO2 sensors, in a single line from the center of the wound contact layer to the edge thereof, 10 mm pitch), tissue color (e.g., 10 optical sensors, in 2×5 array, ~20 mm pitch, electrical stimulation (e.g., electrodes), patient movement (e.g., an accelerometer, electromyography (EMG), magnetometer, gyroscope), pH (e.g., by measuring color of a pH-sensitive pad, optionally using the same optical sensors as for tissue color), and conductivity (e.g., 9 conductivity contacts, in a 3×3 array, ~40 mm pitch). In some instances, more or fewer than five sensors can be utilized. Not all 5 sensors in each row of the array need be aligned. In some instances, all the sensors can be of the same type. In other instances, two or more different types of sensors can be used. In some embodiments, the sensors can include at least one nanosensor, thermistor, conductivity sensor, Sp02 sensor, pH sensor, color sensor, optical sensor, impedance sensor, and/or electrode. In some embodiments, the sensors can include optical, thermistors, and/or impedance sensors. In some embodiments, the sensors can include optical, thermistors, impedance sensors, and/or any other sensor types described herein. In some embodiments, the impedance sensor could be an electrode that measures impedance or conductivity. The impedance sensor can include multiple electrodes. In some embodiments, the optical sensor can include an LED and an optical sensor. The optical sensor can comprise at least one of a red, green, blue, and clear (RGBC) sensor or red, green blue, and white (RGBW) sensor.

SpO2 is an estimate of arterial oxygen saturation. As shown in FIG. 3A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, and/or on intact skin to measure changes between the various regions. In some embodiments, the wound contact layer and/or sensor array can be larger than the size of the wound to cover the entire surface area of the wound as well as the surrounding intact skin. The larger size of the wound contact layer and/or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester (PET), polyethylene naphthalate (PEN), polyetherimide (PEI), along with various fluropolymers (FEP) and copolymers, and/or any material known in the art. The sensor array can be incorporated into a two-layer flexible circuit. In some embodiments, the circuit board can be a multi-layer flexible circuit board. In some embodiments, these flexible circuits can be incorporated into any layer of the wound dressing. In some embodiments, a flexible circuit can be incorporated into a wound contact layer. For example, the flexible circuit can be incorporated into a wound contact layer similar to the wound contact layer described with reference to FIGS. 2B and 2C. The wound contact layer can have cutouts or slits that allow for one or more sensors to protrude out of the lower surface of the wound contact layer and contact the wound area directly.

In some embodiments, the sensor integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressing or one or more components forming part of an overall wound dressing apparatus. The upper surface of the first wound contact layer and the lower surface of the second wound contact layer can be adhered together with the flexible circuit board sandwiched between the two layers.

In some embodiments, the one or more sensors of the flexible circuit board can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 3H are shown protruding out the bottom surface of the wound contact layer. In some embodiments, the SpO2 sensors can be mounted directly on a lower surface of the first wound contact layer. Some or all of the sensors and electrical components may be potted or encapsulated (rendered waterproof) with a polymer, for example, silicon or epoxy based polymers. The encapsulation with a polymer can prevent ingress of fluid and leaching of chemicals from the components. In some embodiments, the wound contact layer material can seal the components from water ingress and leaching of chemicals.

The information gathered from the sensor array and associated wound dressing system can utilize three major components, including a sensor array, a control module, and software. These components are described in more detail below.

As described above, the sensor array of FIG. 3A can include a thermistor 321, conductivity sensor 324, optical sensor 323, and SpO2 322 sensor. The flexible sensor array circuit board 300 includes a sensor array portion 301, a tail portion 302, and a connector pad end portion 303 as shown in FIG. 3B. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound and in a more convenient location. An overall view of one of the sensor arrays circuit board 300 is shown in FIG. 3B.

Figure 3D:
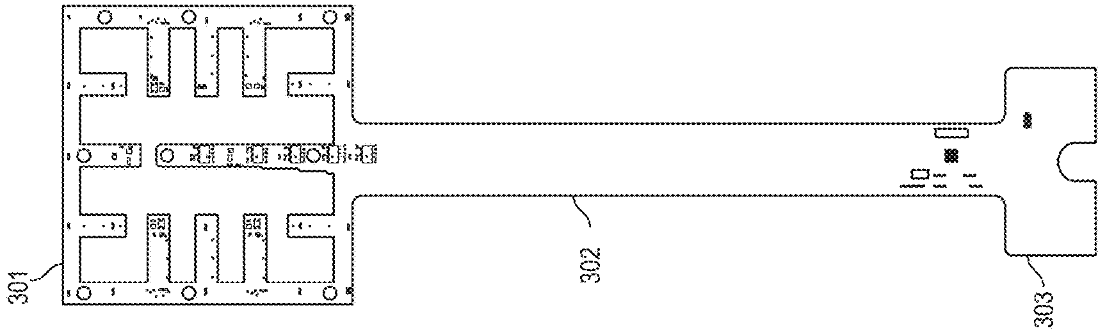
Figure 3C:
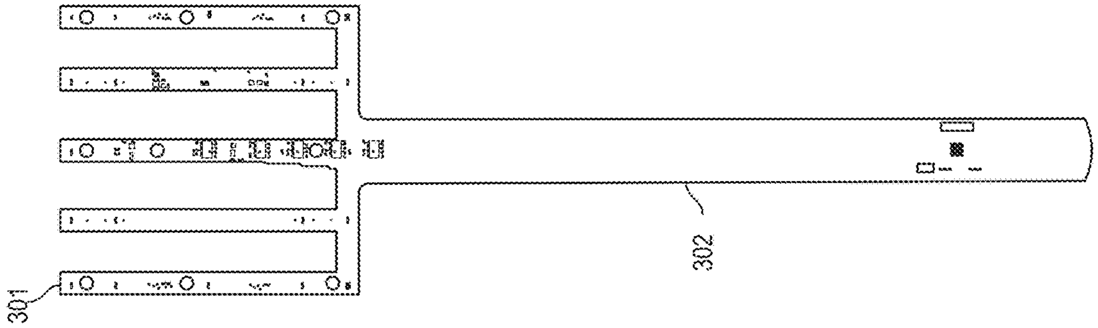

FIGS. 3C-3F show embodiments of the flexible circuit boards with four different sensor array geometries. The four different sensor array geometries shown are implemented in flexible circuits. While FIGS. 3C-3F show four different sensor array formats and configurations, the design as shown in FIG. 3D also shows the connector pads end portion 303. However, the designs of FIGS. 3C, 3E, and 3F can also be created with the connector pads end portion 303 to allow these flexible circuit boards to communicate with a control module or other processing unit. FIG. 3C-3F illustrate four different sensor array geometries in the sensor array portion 301.

Figure 3G:
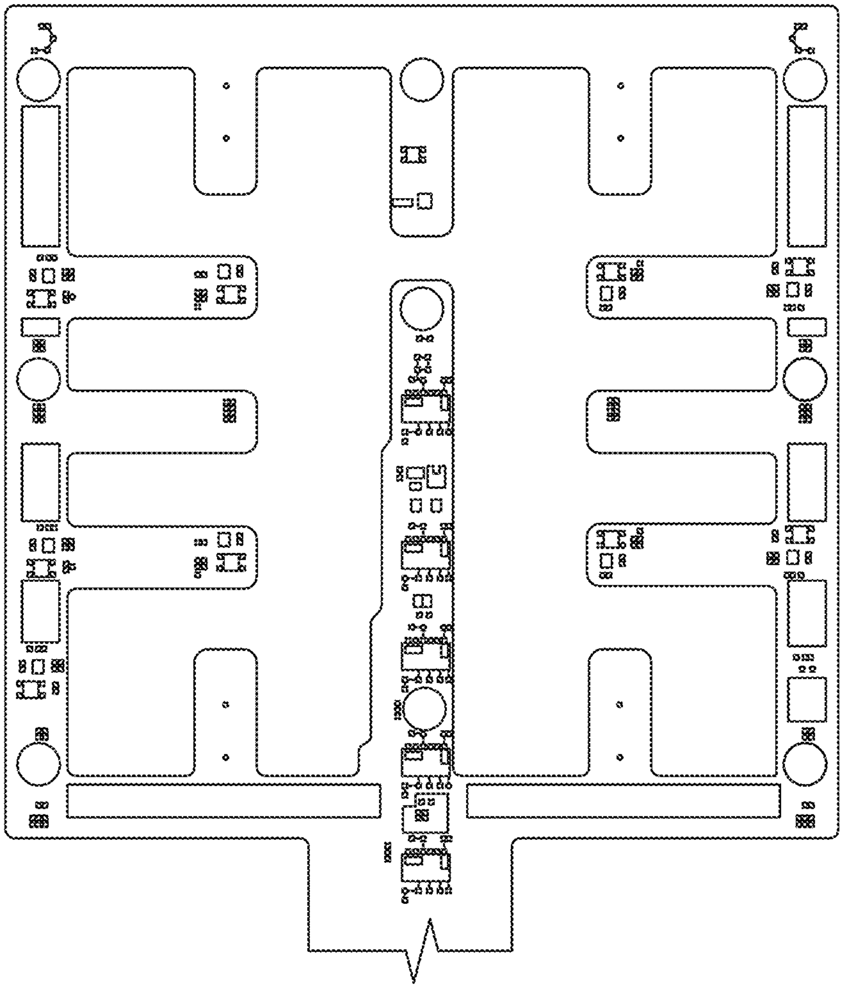
FIG. 3G shows an embodiment of the sensor array portion 301 of the sensor array design shown in FIG. 3D in more detail.
Figure 3H:
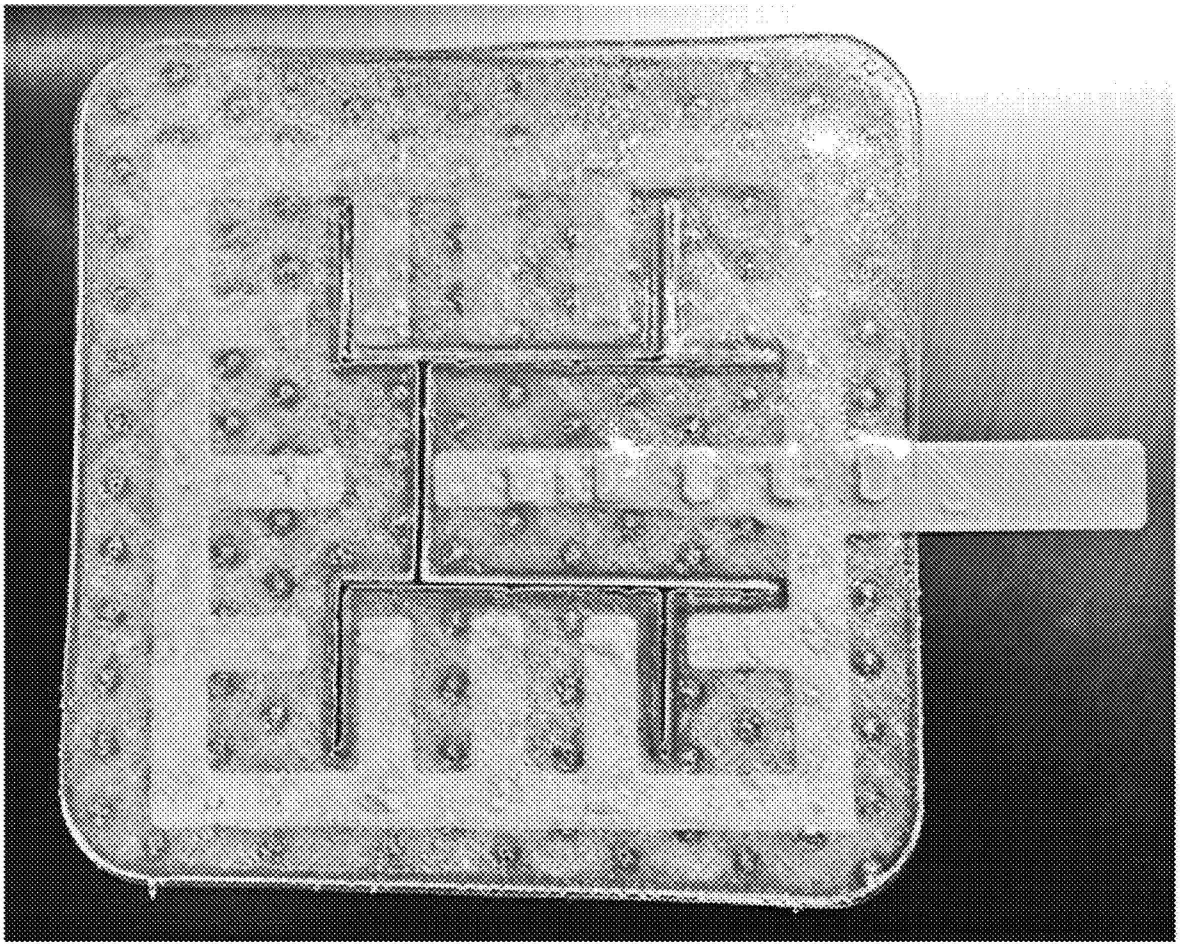
FIG. 3H illustrates a flexible sensor array incorporated into a perforated wound contact layer according to some embodiments.

FIG. 3G shows an embodiment of the sensor array portion 301 of the sensor array design shown in FIG. 3D in more detail. In the embodiments of FIGS. 3A-3G, it will be appreciated that the sensor array portion 301 includes a plurality of portions that extend either around a perimeter of a wound dressing component such as a wound contact layer, or inward from an outer edge of the wound dressing component. For example, the embodiments illustrated include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 3A, this allows some, and possibly a majority of the wound dressing component to be uncovered by the sensor array. For example, for a perforated wound contact layer as shown in FIGS. 3A and 3H, the sensor array portion 301 may not block a majority of the perforations in the wound contact layer. In some embodiments, the sensor array may also be perforated or shaped to match the perforations in the wound contact layer to minimize the blocking of perforations to fluid flow.

Connectivity for the sensor array can vary depending on the various sensors and sensor array designs utilized. In some embodiments, as shown in FIG. 3C-3F, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, thermistors, conductivity sensors, SpO2 sensors, and/or color sensors can be used on the sensor array to provide information relating to conditions of the wound. The sensor array and individual sensors can assist a clinician in monitoring the healing of the wound. The one or more sensors can operate individually or in coordination with each other to provide data relating to the wound and wound healing characteristics.

Temperature sensors can use thermocouples and/or thermistors to measure temperature. The thermistors can be used to measure and/or track the temperature of the underlying wound and/or the thermal environment within the wound dressing. The thermometry sensors can be calibrated and the data obtained from the sensors can be processed to provide information about the wound environment. In some embodiments, an ambient sensor measuring ambient air temperature can also be used to assist in eliminating problems associated with environment temperature shifts.

Optical sensors can be used to measure wound appearance using an RGB sensor with an illumination source. In some embodiments, both the RGB sensor and the illumination source would be pressed up against the skin, such that light would penetrate into the tissue and take on the spectral features of the tissue itself.

Light propagation in tissue is dominated by two major phenomena, scattering and attenuation. For attenuation, as light passes through tissue, its intensity is lost due to absorption by various components of the tissue. Blue light tends to be attenuated heavily, whilst light at the red end of the spectrum tends to be attenuated least.

Scattering processes are more complex, and have various 'regimes' which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart-so a 1 mm path distance would effectively randomise the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofloresence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue and/or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size and/or wound shape change. In some embodiments, the conductivity sensors can be used in the wound bed and/or on the perimeter of the wound.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

FIG. 3H illustrates a flexible sensor array incorporated into a perforated wound contact layer according to some embodiments. As shown in FIG. 3H, the PCB sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

Figure 3I:
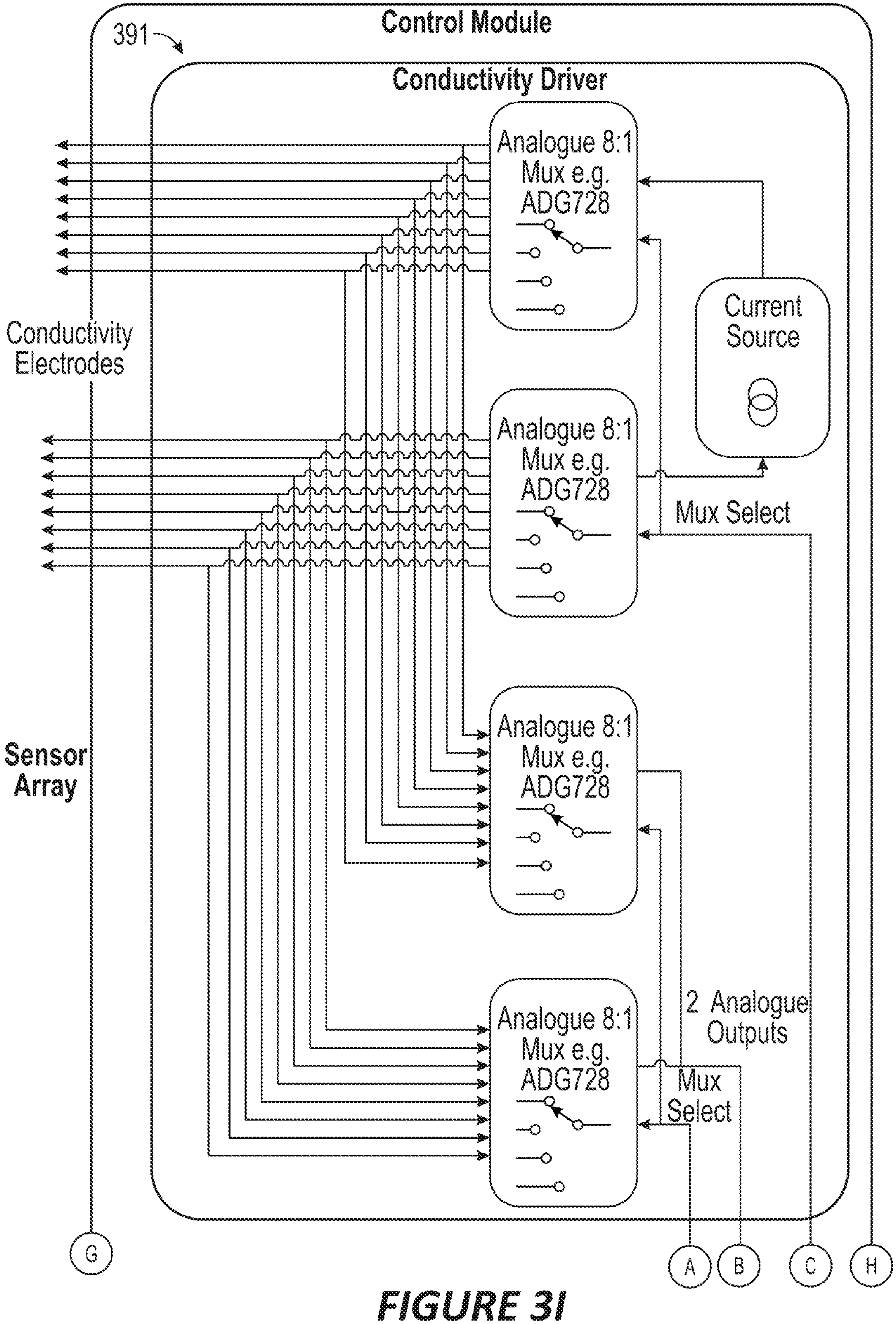
FIG. 3I illustrates a block diagram of a control module according to some embodiments.
Figure 3I:
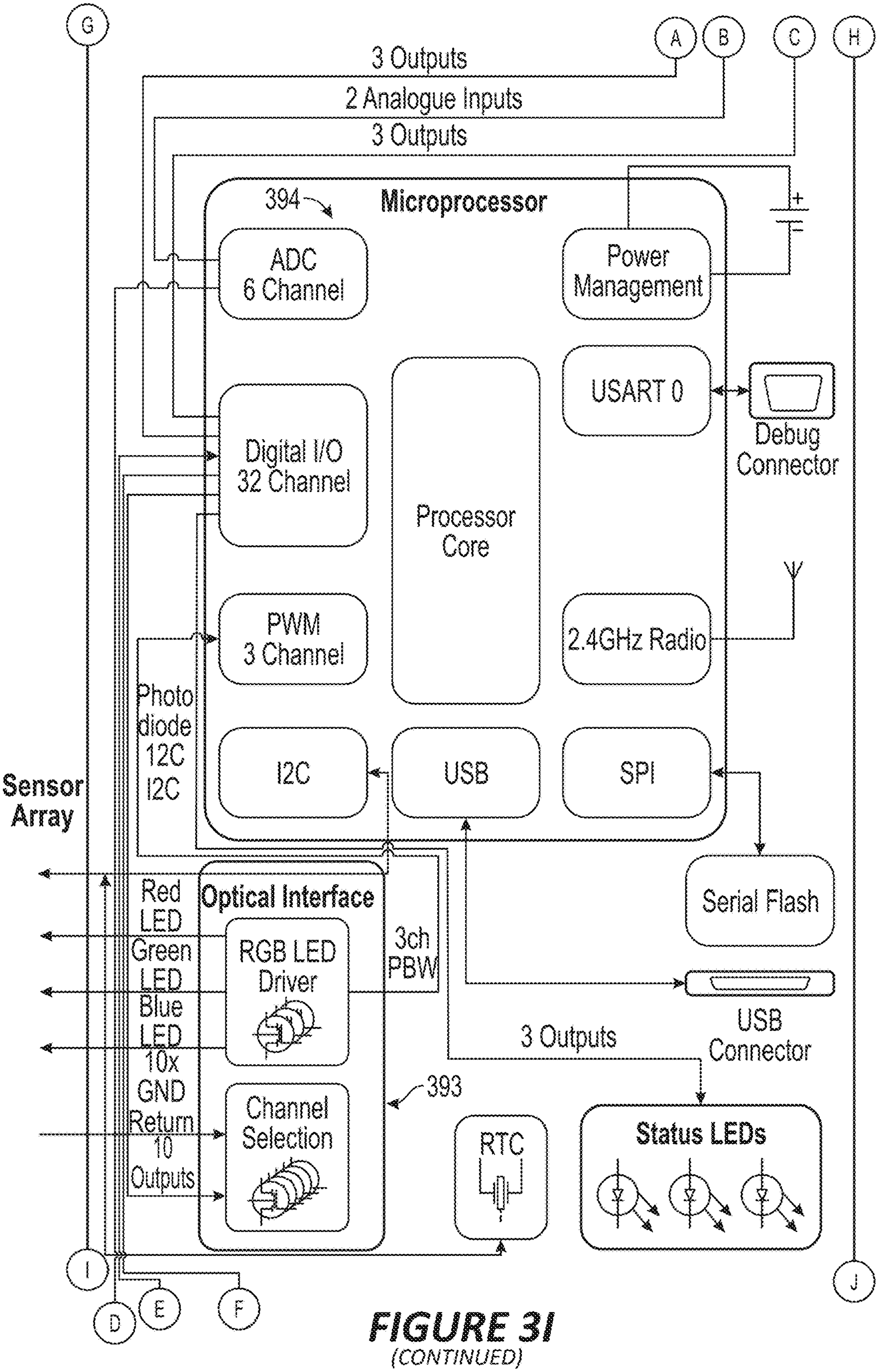
Figure 3I:
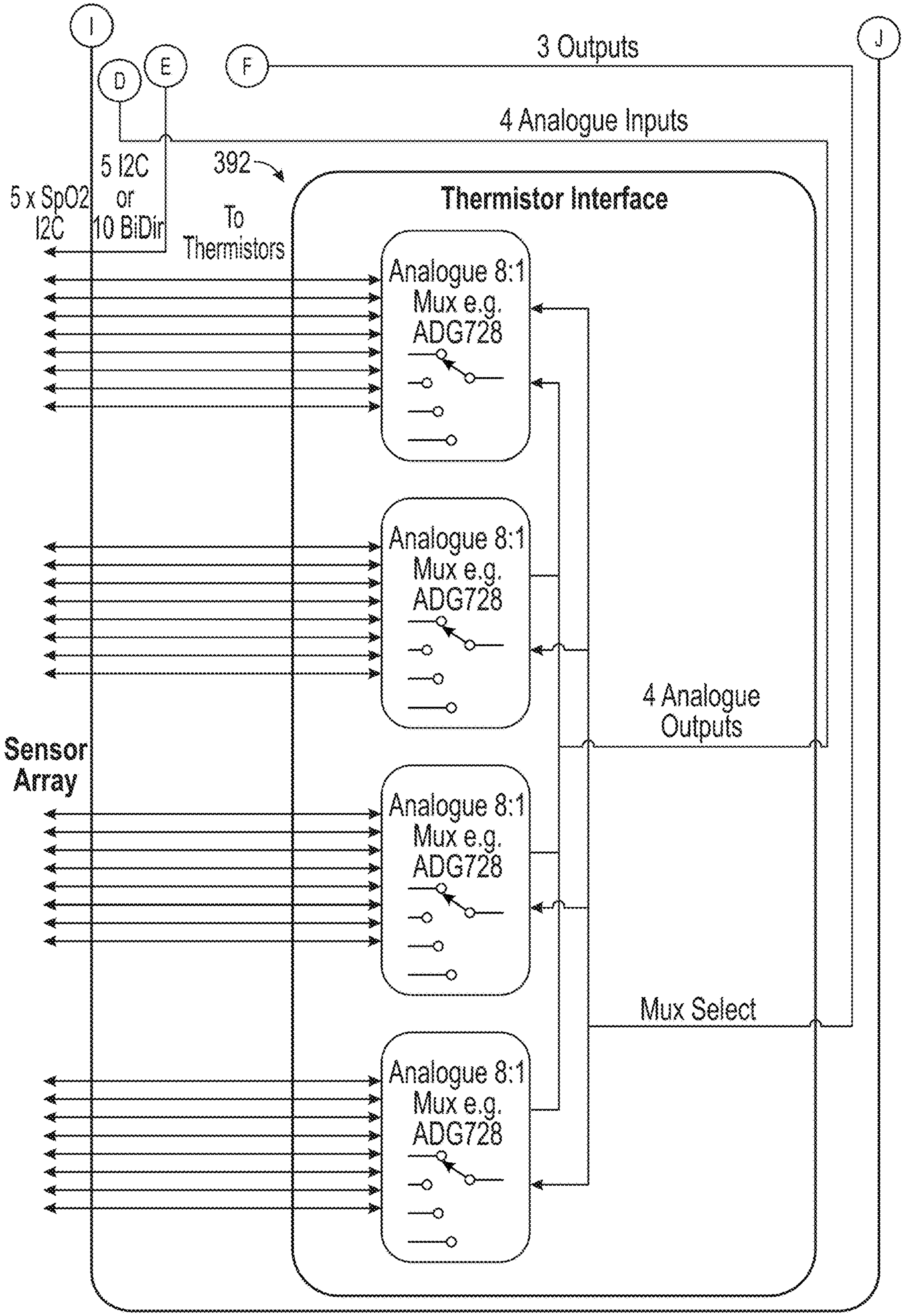

FIG. 3I illustrates a block diagram of a control module according to some embodiments. The block diagram of the control module includes a conductivity driver box 391 displaying features of the conductivity driver. Box 392 shows the features of the thermistor interface and box 393 shows the features of the optical interface. The control module can include a microprocessor with features similar to those shown in box 394. Real time clock (RTC), Status LEDs, USB connector, Serial Flash, and Debug Connector can be included as features of the control module as shown in FIG. 3I.

In some embodiments, the microprocessor can have one or more of the following requirements: 2.4 GHz radio (either integrated, or external); Supplied Bluetooth software stack; SPI interface; USB (or UART for external USB driver); I2C; 3 channel PWM; 32 GPIO; and/or 6-channel ADC. In some embodiments, the device can require at least 48 I/O pins or possibly more due to banking limitations. Bluetooth stack typically requires ~20 kB on-board Flash, so a minimum of 32 KB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

In some embodiment, the control module can implement a memory component where the amount of local storage depends on the sample rate and resolution of the sensors. An estimated data requirement of 256 Mb (32 MB) is available in a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051HR can be used. Based on the initial system architecture, 8 of these will be required.

The control module can incorporate a battery. For example a 300 mWh/day battery can be used. For 7 days this is 2100 mWh. This could be provided by: a 10 days, non-rechargeable, ER14250 (14.5 mm diameter×25 mm) LiSOCl2 cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by a host software. The software may be executed on a processing device. The processing device can be a PC, tablet, smartphone, or other computer capable of running host software. The processing device executing the software can be in communication with the control module through electrical wires and/or through wireless communication. This software is not to perform the big-data analysis, but to provide access to the data held on the control module. Analysis software is beyond the scope of this document. The host software can include an interface to the control module via Bluetooth and/or USB. In some embodiments, the host software can read the status of control module, download logged data from control module, upload sample rate control to control module, convert data from control module into format suitable for processing by big-data analysis engine, and/or upload data to cloud for processing by analysis engine.

The software may be developed for PC (Windows/Linux), tablet or smartphone (Android/iOS), or for multiple platforms.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, and/or adjacent to the backing layer. In some embodiments, the wound dressing can include a second cover layer and/or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Sensor Placement

Accurate placement of a sensor or a sensor array can be important to effective treatment of a wound or to effective data gathering. For example, different locations in and around wound can have drastically different characteristics. Without knowing where a sensor is located (for example, relative to the wound, other sensors, the patient, etc.), measured data can be misleading or inaccurate, thereby making it difficult to provide effective treatment to a patient. Accordingly, in some embodiments, one or more techniques are utilized to assist in increasing the accuracy of the sensor data. For example, one or more techniques are provided for reducing the chances of imperfect or incorrect placement. In addition, one or more techniques are provided for increasing the accuracy of sensor data despite imperfect or incorrect placement. Similarly, one or more techniques are provided which do not require specific, precise placement of sensors to gather accurate information.

In some embodiments, the position or orientation of one or more sensor strings, sensor strips, sensor arrays, or sensor matrices (generally referred to as sensor package), wounds, wound dressings, wound fillers, wound dressing apparatuses, etc. is tracked or determined and may be utilized to limit orientation errors. For example, alignment or orientation considerations may be taken with respect to how a sensor package is placed in or onto the wound to ensure that when the sensor package is installed or replaced, its orientation in each case is known. This can be necessary to co-reference and cross-reference data. In addition, the position or orientation data can be utilized to assist in the placement (e.g., initial placement or subsequent adjustments) of a wound dressing or sensor package to lessen the likelihood of imperfect placement. In addition, sensor data or sensor functionality can be modified based on the position or orientation data in order to increase the accuracy of sensor data despite imperfect placement.

In some embodiments, a sensor package can be utilized to limit orientation errors. For example, it may prove difficult to place a single sensor in a desired location because, for instance, the sensor may be small or difficult to orient correctly. A sensor package, on the other hand, can be easier to orient because, for example, the increased size or potential for orientation markers, as described herein.

In some embodiments, sensors or sensor package can be incorporated into or encapsulated within a wound dressing or wound packing material. For example, the sensors may be stitched into or otherwise permanently or semi-permanently attached to gauze or durafibre or one or more layers of the wound dressing. As another example, the sensors may be mounted onto foam protrusions which fit into wound. Still, in another example, a sensor or sensor package may be deployed into an expandable matrix, foam or other material which fills the wound.

Alignment Features

Figures 4A, 4B, 4C:
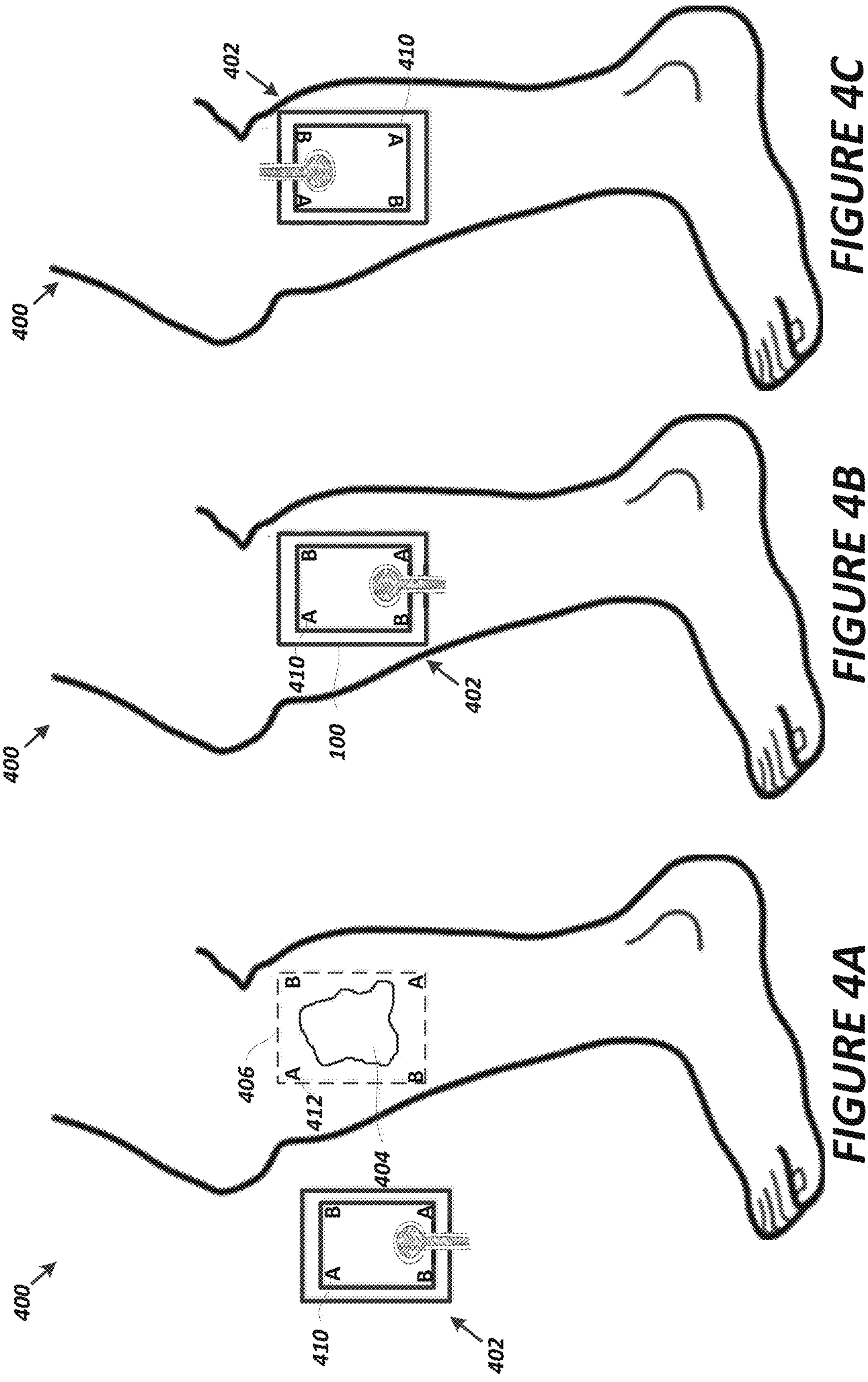
FIGS. 4A-C illustrate embodiments of a negative pressure wound therapy (NPWT) system having a plurality of alignment features for assisting in proper placement of a wound dressing on a wound.

FIGS. 4A-C illustrate diagrams of a negative pressure wound therapy (NPWT) system 400 having a plurality of alignment features 406, 410, 412 for assisting in proper placement of a wound dressing 402 in or on a wound 404 according to some embodiments. The system 400 includes a wound dressing 402 which can be any wound dressing as described herein, such as wound dressing 100 of FIGS. 1A-1B. In addition, the system 400 can include a pump (not shown) connected to the wound dressing, as described herein. The one or more alignment features 406, 410, 412 can be included on the wound dressing or an area around the wound and can help reduce a likelihood of an imperfect or incorrect placement of a wound dressing 402 on the wound 404.

FIG. 4A illustrates a wound dressing 402 prior to its placement in or on a wound 404. FIGS. 4B-4C illustrate a properly positioned wound dressing 402 in or on the wound 404 using one or more alignment features 406, 410, 412. As illustrated, the alignment features include an alignment ring 406 and orientation features 410, 412. However, it should be noted that one or more other alignment features can be used in addition or alternatively. For example, other alignment features can include a full or partial image or diagram of a patient. For instance, the wound dressing is correctly oriented when the orientation of the patient in the diagram matches the orientation of the patient. In addition, alignment features can include corner indicators which indicate an area of location for placement of the wound dressing corners. Alignment features can also include anatomical feature indicators. For instance, an arrow or other directional element is on the wound dressing and will point to a particular location (e.g., a patient's left foot) when positioned correctly. In some embodiments, alignment features can also include a pattern or other marking which can indicate a correct orientation of the wound dressing. For example, the alignment features can include a plurality of blocks placed in a corner of the wound dressing. The wound dressing is oriented correctly when the blocks are in the top left corner. The alignment features can also include an orientation indicator such as an accelerometer, orientation sensor, gravity sensor or level. For example, the alignment feature can include a sealed chamber or bubble with fluids of different densities (e.g. air bubble in saline). The orientation or position of the fluids can indicate the orientation of the wound dressing. The one or more alignment features can assist in guiding a patient or caregiver in the placement or replacement of wound dressings, wound filling material, sensors, or sensor packages. As described herein, one or more sensors can be integrated into a sensor package, a wound dressing, wound filling material, etc. Similarly, a sensor package can be integrated into a wound dressing or wound filling material.

The alignment ring 406 can be configured such that when the wound dressing 402 is aligned (e.g., fits within, matches, or corresponds) with the alignment ring, the wound dressing or any sensors integrated in the wound dressing are properly positioned. The alignment ring 404 may be semi-permanently attached to or printed in or around the wound 402 to allow wound dressing 401 to be accurately placed or replaced in a desired position. The alignment ring can be any semi-permanent or permanent visual or other indicator which can assist in the placement of the wound dressing 402. For instance, the alignment features can be a temporary tattoo, ink (e.g. invisible ink), tape, sticker, anatomical feature, etc.

Although the alignment ring 406 is illustrated having a rectangular shape, it will be appreciated that the alignment ring 406 can take any shape including other shapes such as rectangular, circular, oval, etc. In some embodiments, the shape of the alignment ring advantageously matches the shape of the wound dressing 402 to allow for easy and accurate placement. However, in some instance, the shape of the alignment ring 406 is different from the shape of the wound dressing 402.

In some embodiments, other alignment features are utilized in addition to or instead of the alignment ring 406. For example, an indicator which indicates the desired position of an edge, corner, or sensor can be utilized. As a non-limiting example, the alignment features can include two or more corner indicators, such that when corners of the wound dressing 402 are positioned at the corner indicators, the wound dressing is accurately placed. As another example, the alignment features can be included on the wound dressing 402 and can correspond to an anatomical feature of the patient. For example, the wound dressing 402 can include an arrow designed to point at an anatomical feature (e.g., a patient's head), when properly aligned.

In some embodiments, a patient, caregiver, computer guided apparatus, etc. can draw, place, stick, or otherwise position one or more alignment features on a wound dressing, sensor, sensor package, or a patient's body to assist in the positioning of the wound dressing or sensors. In other instances, the alignment features can be projected (such as with a light source) or seen using a form of virtual or augmented reality.

In some instances, the alignment features are determined prior to placement of the wound dressing 402. For example, a computing system or physician can determine where an alignment ring should be placed on a patient based at least in part on known sensor positioning within the wound dressing. As another example, the position or orientation of the alignment features can be determined based at least in part on the size, location, shape, depth, etc. of the wound. Alternatively or in addition, the position or orientation of the alignment features can be determined based at least in part on the type(s) of sensors to be used in the wound dressing.

In some embodiments, the alignment features can be determined after the wound dressing or sensors have been attached to or placed on the patient for a first time. For example, in some instances, wound dressings may require periodic replacement. In examples such as these, the wound dressing can be initially placed in or on a wound without utilizing any alignment features. For instance, as described herein, a wound dressing or sensor may not require specific placement in or on the wound. Instead, the individual sensor components may have a means of registering their position with respect to each other in order to understand their position within a wound. However, when the wound dressing is replaced with a new wound dressing, it can be desirable (for example, for data accuracy or consistency) to place the new wound dressing in the same or substantially same location as the old wound dressing. Accordingly, in some embodiments, the alignment features can be determined after the initial placement and position registering of the sensors. For example, an outline or other indication of the wound dressing can be marked on the patient's body. Subsequently, when the wound dressing is replaced, a new wound dressing can be accurately placed using the alignment features.

In some embodiments, to further reduce a likelihood of imperfect or incorrect placement, a wound dressing or sensor package may be at least partially rotationally symmetric, such that the accuracy of the sensors will not be impacted by rotational misalignment. In some embodiments, rotationally symmetric means that the sensors are rotationally symmetrically positioned in the wound dressing or sensor package such that, when rotated by a certain degree, sensors of the same type remain positioned in the same locations. For example, wound dressing 402 illustrated in FIGS. 4A-4C includes orientation marks (A, B, B, A) 410 which correspond to orientation marks (A, B, B, A) 412 at the wound 404. As illustrated by FIGS. 4B and 4C, because the wound dressing 402 is rotationally symmetric, the wound dressing can be accurately positioned despite whether it is oriented as illustrated in FIG. 4B or as illustrated in FIG. 4C. Note that orientation marks 410 and 412 are matched (e.g., A corresponds to A, B corresponds to B, etc.) in both orientations.

Position or Orientation of Sensors

In some embodiments, a system (such as, an NPWT system) can utilize a signal emitting device or position sensing unit to track the position or orientation of sensors, estimate movement, position, or location of the wound, patient, etc. For example, the system can include sensors which can continually, or repeatedly, report or receive position or orientation data to, for instance, one or more other sensors. In addition or alternatively, the system can utilize sensor packages in which the position or orientation of each sensor on sensor package is known, and a single or a few sensors can be used to register the location of the sensor package.

As described herein, position or orientation (also referred to as emplacement) considerations may be taken with respect to how one or more sensors are placed in or onto the wound to ensure that when the one or more sensors are installed or replaced, their orientation in each case is known. The term emplacement as used herein may refer to, without limitation, position or orientation or any other appropriate location information. These placement considerations can be desired, for instance, to co-reference and cross-reference data such that the position of each sensor relative to, for instance, a wound, can be determined. For example, the individual sensor components may have a means of registering their position with respect to each other in order to understand or record position on or within a wound.

The position or orientation of a sensor, sensor package, or wound dressing can be tracked or determined using a variety of techniques. For example, in some embodiments, an emplacement sensor can be integrated into a sensor package, wound dressing, etc. and a position sensing unit can track a position or orientation of an emplacement sensor within a tracking area. The position tracking unit can then provide positioning data to a processor, such as a processor of a NPWT system or a remote processor, which can co-reference or cross-reference data from other sensors. Alternatively, a processor can co-reference or cross-reference the received emplacement data with known emplacement data (such as the position or orientation of each sensor in the sensor package) to determine additional emplacement information.

As a non-limiting example, an emplacement sensor can be communicatively coupled to a position sensing unit. The position sensing unit can be part of a wound dressing or it can be a separate component. The position sensing unit can be used to determine the emplacement of the emplacement sensor or a set of sensors (for example, a sensor array). For example, the position sensing unit can determine the pose of the emplacement sensor relative to a room coordinate system. The pose and the room coordinate system can then be utilized to determine a pose of other sensors.

In some embodiments, the position sensing unit can include one or more sensing devices such as the HiBall tracking system, a GPS device, or signal emitting device that would allow for tracking of the emplacement of the emplacement sensor. In some embodiments, a position sensing unit can be affixed to a wound dressing. The wound dressing apparatus can be tracked by the position sensing unit. A room coordinate system reference can also be tracked by the position sensing unit in order to determine the emplacements of the sensors or the wound dressing with respect to the room coordinate system. In some embodiments, the wound dressing can also include or have coupled thereto one or more accelerometers, which can also be used to estimate movement, position, and location of the wound, patient, etc.

As another example, position or orientation of a sensor can be determined using a signal emitting device that includes, for instance, a radio-frequency identifier (RFID). In such embodiments, a position sensing unit can use GPS coordinates of the one or more tracking units or can, for example, triangulate the radio frequency signal being emitted by the RFID associated with the one or more tracking units to determine an emplacement of the wound dressing, sensors, etc. Alternatively or in addition, the sensor package may register itself with electromagnetic tags (e.g. RFID tags) placed on or near the patient that allow the sensor package to define its position and orientation with respect to the tags.

In some embodiments, the emplacement of one or a few sensors is tracked or determined, and known relationships are used to determine other emplacement data (e.g., emplacement data of other sensors, the wound dressing, the wound, the patient, etc.). As described herein, one or more sensors can be incorporated into a sensor package such as a sensor string, a sensor strip, a sensor array, a sensor matrix, or a flexible circuit board. Alternatively or in addition, one or more sensors can be incorporated into a wound dressing or wound filler. The position of the sensors in the sensor package, wound dressing or wound filler may be known and relationships between other sensors, wound location, etc. can be determined.

A system, such as a negative pressure wound therapy (NPWT) system, can determine the emplacement of a first sensor and then, based at least in part on the determined placement of the first sensor and a known relationship between the first sensor and other sensors, can determine an emplacement of the other sensors. Alternatively, in some embodiments, the system can determine an emplacement of the entire sensor package and use the emplacement data of the sensor package, as well as a known relationship, to determine the emplacement of one or more sensors on the sensor package. Still, in other embodiments, the emplacement of several or all the sensors can be tracked or determined. In some instances, the system can determine the emplacement of each sensor using more than one technique described herein (e.g., tracking the sensor, determining based on a known relationship, etc.). The system can suitably arbitrate between emplacement determined using multiple techniques and can determine if an emplacement is perceived to be inaccurate or unreliable.

Figure 5:
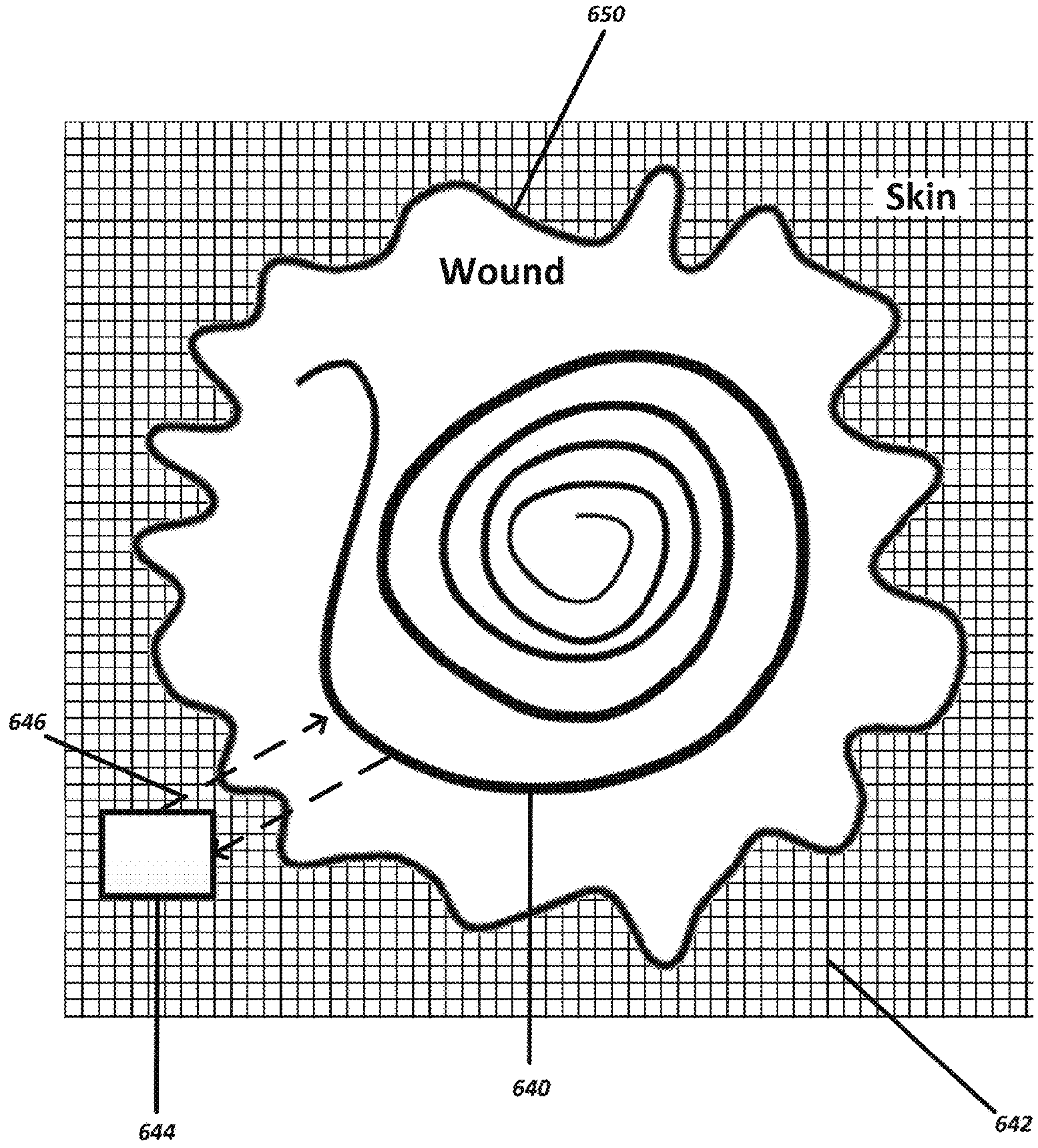
FIG. 5 illustrates a system having a strip of sensors positioned in a wound, according to some embodiments.

FIG. 5 illustrates a system having a string or strip 640 of sensors positioned within a wound 650, according to some embodiments. In some implementations, the placement of the strip 640 can require specific placement such that it should be placed by a physician or other qualified personnel. Alternatively, in certain cases, the strip 640 may not require a specific placement, and the strip 640 may be placed by any individual, such as a physician, nurse, caregiver, or the patient. In some embodiments, the strip 640 of sensors may not be a strip, but is instead another sensor package or a plurality of individual or coupled sensors.

In some embodiments, the system can include a component 644 which can reside outside the wound, such as on the skin 642 (for example, the skin at the wound) or in a wound dressing, and can communicate 646 with the sensor strip 640. In some embodiments, the position or orientation of the component 644 can be a known input of the system. As such, the position of the component 644 can be utilized to determine the position or orientation of the sensor strip 640 or specific sensors of the strip. The component 644 can be a position sensing unit or any other positioning or locating module described herein. In certain cases, the component 644 is optional.

In some embodiments, the position or orientation of a sensor, sensor package, wound dressing, etc. can be determined using a camera or other recording device as described herein. For example, one or more pictures or videos may be taken of the wound prior to the filling of the wound with filling or packing material, after the filling of the wound packing material, after the placement of the sensors, or after the placement of the wound dressing. The images can allow the orientation of the sensors, wound dressing, etc. to be calculated after placement. The image or video may, in some embodiments, be performed in concert with the sensing elements performing an action. For example, the image or video may be performed in concert with lighting up LEDs, together or in sequence, or sensing an external reaction such as a camera flash or one or more external light frequencies.

Sensor Arrays

Figure 6A:
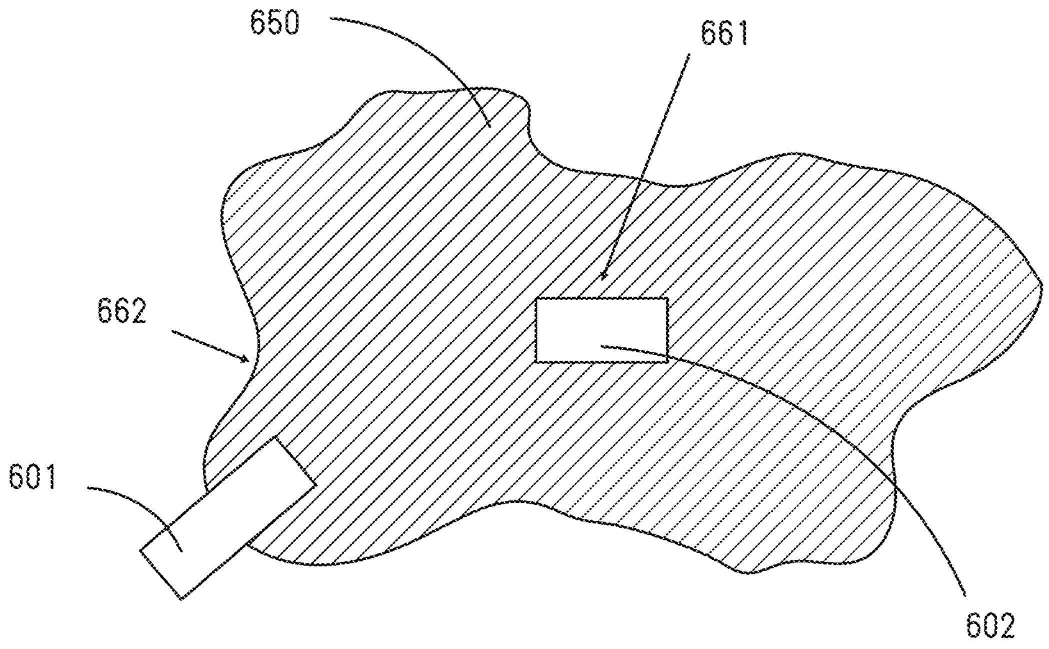
FIGS. 6A-6E illustrate embodiments of sensor positioning in a wound according to some embodiments.

FIGS. 6A-6D illustrate embodiments of sensor positioning in a wound according to some embodiments. FIG. 6A illustrates one or more sensor tags or positioning devices 601 positioned across the edge of the wound according to some embodiments. Sensor tag as used herein can refer to sensor arrays. The sensor tags can be small strips of material with a limited number of sensors on the material. In some embodiments, the sensor tags can include sensors that are positioned in the wound as well as on the skin surrounding the wound, for example, on the periwound. In some embodiments, the sensor tag can be a positioning device that is used to orient and/or determine the position of sensors within the dressing. The sensor tags are similar to the sensor arrays described with reference to FIG. 3A-3H but the sensor tags can be a smaller size and located within a distinct area of the wound as opposed to covering a majority of or large portion of the wound. The sensor tags can be used to gather the same or similar data as described for the sensor arrays described with reference to FIGS. 3A-3I herein and as disclosed in International Patent Application No. PCT/IB2017/000693 incorporated herein as Appendix A. FIG. 6A illustrates embodiments of sensor layouts for the sensor tags.

In some implementations, a sensor tag can be same or similar as the component 644. The one or more sensor tags 601 can extend from the periwound area or an area outside the wound area into the wound area. In some embodiments, an optional second mid-wound sensor tag 602 can be provided within the wound area (for example, inside the perimeter of the wound).

Figure 6B:
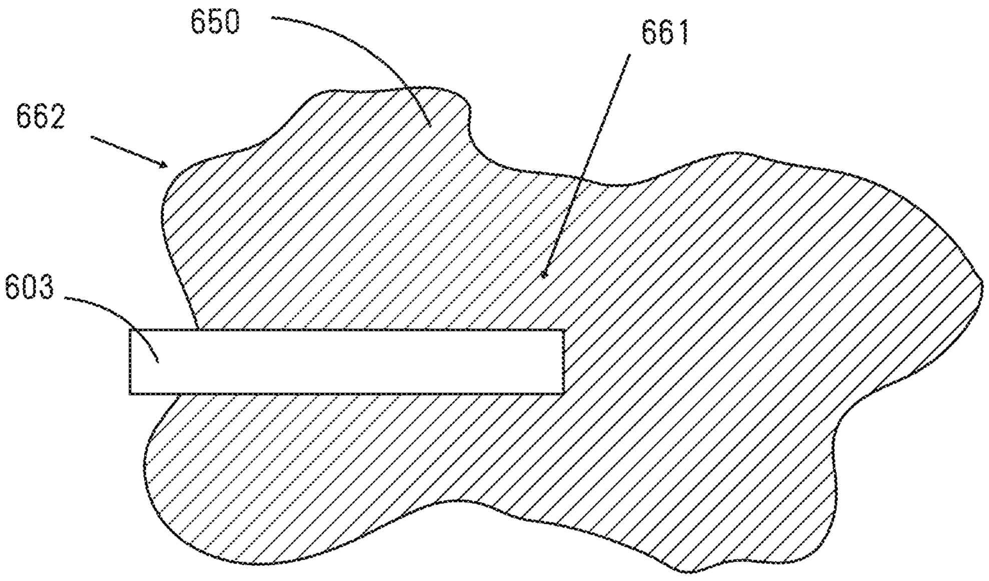

FIG. 6B illustrates a sensor strip 603 positioned across the edge of the wound according to some embodiments. The sensor strip 603 can be a material structure with various sensors positioned along the material. In some embodiments, the sensor strips can be made of thin films. In some embodiments, the thin films can be extensible. For example, suitable films can include polyurethane (PU) and polyethylene (PE, PET) films. Additionally, in some embodiments, woven materials, gauze, nets, non-woven materials, and/or paper could be used. In some embodiments, thermoplastic polyurethane (TPU), silicone, stainless steel (such as, 316), PU, PET, polyphenylene sulfide (PPS), acrylated urethane, and/or acrylated epoxy can be used to form the sensor strips. The sensor strip can extend from the periwound area to the central portion of the wound as shown in FIG. 6B. In some embodiments, the sensor strip 603 can be augmented with an additional sensor tag, for example, a sensor tag similar to the sensor tag 601 in FIG. 6A. In some embodiments, the sensor strip 603 can include positioning device integrated into the strip.

The sensor tag 601 and 602 and sensor strip 603 can utilize the same materials and sensors but can be used to sense characteristics of different area of the periwound and wound. Sensor tag 601 is positioned at a wound edge 662 and therefore can be a sensor cluster at the wound edge. Sensor tag 602 is positioned in the center of the wound 661 and can be a sensor cluster at the wound center 661. Sensor strip 603 as illustrated in FIG. 6B can combine both the sensor at the wound edge 662 and wound center 661 (or close enough) in a single package. Additionally, the sensor strip 603 can extend across the wound from periwound area through the wound to periwound area or any portion thereof as illustrated in FIG. 6E.

Figure 6C:
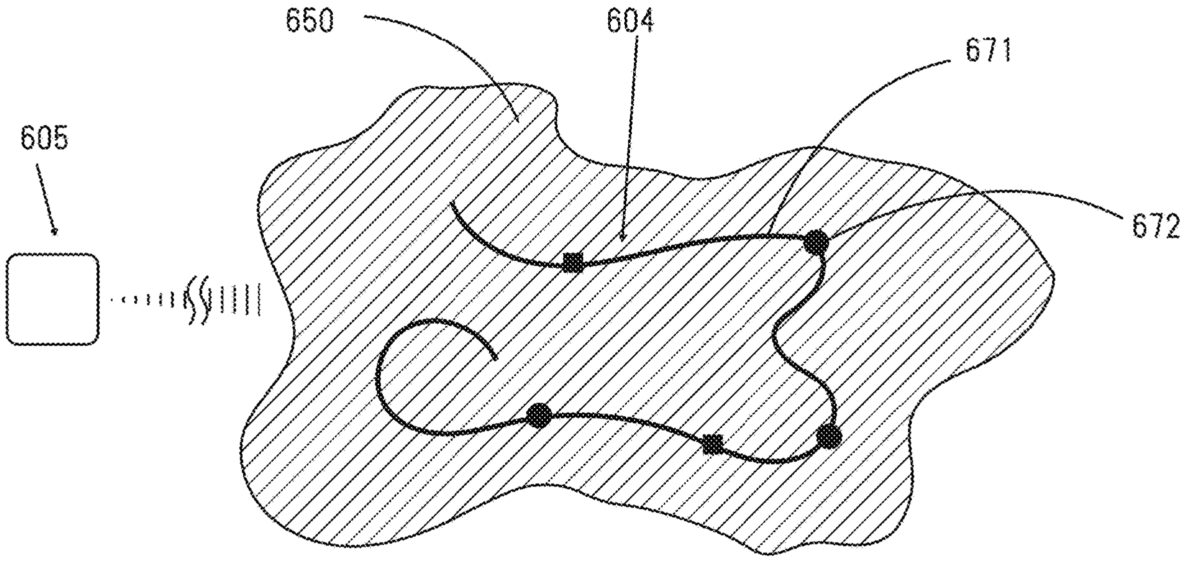

FIG. 6C illustrates a string of sensors 604 to be placed in the wound according to some embodiments. The string 604 can be similar to the string of sensors described with reference to FIG. 5. The string of sensors 604 can be placed in the wound 650 by a clinician or other user. In some embodiments, the string of sensors does not require specific placement. In some embodiments, the string of sensors 604 can include a string or thin material 671 with one or more sensors 672 on the string 671. The string of sensors 604 may be formed from a thin strip of film or other material. In some embodiments, the string of sensors can have a bundle architecture. For example, the string of sensors can be configured in a rope or cord like structure. The string of sensors 604 can be formed from components that allow a long thin flexible material to be positioned flexibly into a wound 650. In some embodiments, the sensors 672 can be positioned in a pattern on the string 671. In some embodiments, the sensors 672 can be evenly dispersed throughout the string, randomly distributed throughout the string, and/or positioned in only one portion of the string.

In some embodiments, the string of sensors can be a cable made up of a number of filaments each carrying a conductive track. Each filament could be coated with an insulator.

In some embodiments, the string of sensors can be in communication with a component 605 external to the wound area. In some embodiments, the component 605 can be a positioning device similar to the component 644 described with reference to FIG. 5. The component or positioning device 605 can reside outside the wound, such as on the skin of the patient (for example, the skin at or around the wound) or in a wound dressing, and can communicate with the sensor string 604. In some embodiments, the position or orientation of the component or positioning device 605 can be a known input of the system. As such, the position of the component or positioning device 605 can be utilized to determine the position or orientation of the sensor string 604 or specific sensors of the string. The component or positioning device 605 can be a position sensing unit or any other positioning or locating module described herein. In some embodiments, the component or positioning device 605 can wirelessly communicate with the sensor string 604. In other embodiments, the component or positioning device 605 can be in electrical connection with the sensor string 604. In certain cases, the component or positioning device 605 is optional. In some embodiments, the component or positioning device 605 can include an optical sensor or detector that receives information wirelessly from one or more light sources (LEDs) on, in, or near the wound. In some embodiments, the light sources can be flashing in various colors or patterns to wirelessly communicate information to the imager or receiver.

In some embodiments, the component 605 can be designed to allow for components such as bulky items (e.g. batteries) to be moved out of the wound. In some embodiment, the component 605 or 644 can be used for the sensor tags and sensor strips described with reference to FIG. 6A or 6B. For example, the sensor tags 601 and 602 of FIG. 6A may utilize a component similar to component 605. The component used with the sensor tags 601 and 602 can include a power source, such as a battery or one or more batteries or other electrical components. For example, such other electrical components can include one or more communication modules, processors or an accelerometer.

Figure 6D:
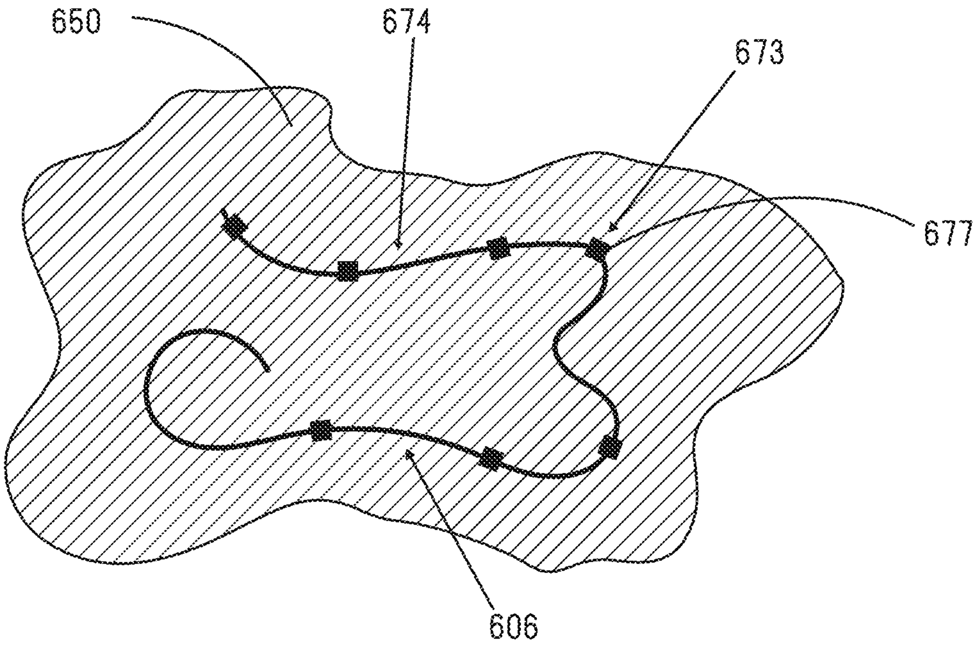
Figure 6E:
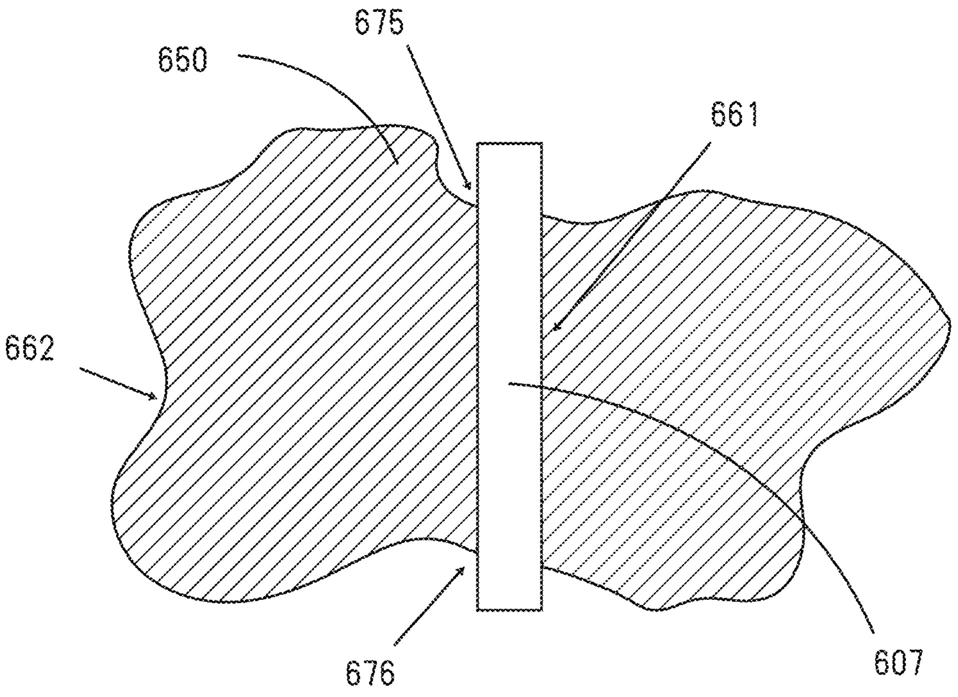

FIG. 6D illustrates a string of sensors 606 for positioning in the wound 650 according to some embodiments. The string of sensors 606 can be similar to the string described in FIGS. 5 and 6C, but the sting of sensors 606 has widened sections 673 and thin sections 674 throughout. In some embodiments, the widened sections 673 are similar to the sensor positioning devices or other sensors described herein. In some embodiments, the widened sections 673 can allow for a larger surface area to position sensors 677 on. In some embodiments, the widened sections 673 can allow for identifiable features that can be used to position and orient the sensor string 606 within the wound area. In some embodiments, the widened sections 673 can include positioning devices to provide information regarding the positioning or orientation of the sensor string 606. In some embodiments, the widened sections 673 can be as wide as required by the sensors that are mounted on them and the narrow sections can be primarily wires and tracks between the elements.

FIG. 6E illustrates an embodiment of a sensor strip 607 that extends across a wound from one side of the wound 650 to another. For example, the sensor strip 607 can run from a first side 675 of the wound to a second side 676 of a wound. In some embodiments, The sensor strip 607 can extend from the first side 675 to an opposite second side 676 and the sensor strip 607 can pass through the center 661 (or close to) of the wound 650 while still being in contact with the wound edge 662 at a first and second side 675 and 676 as illustrated in FIG. 6E.

In some embodiments, sensor elements can include sensors as described herein. For example, the sensor strips and strings can include, an Sp02, RGB, or other elements as well as a light source (e.g. LED). In some instances, all the sensors can be of the same type. In other instances, two or more different types of sensors can be used. In some embodiments, the sensors can include optical, thermistors, and/or impedance sensors. In some embodiments, the sensors can include optical, thermistors, impedance sensors, and/or any other sensor types described herein.

In some embodiments, the light source or other electromagnetic source can be used in combination with an imager or another detector to identify a location of a specific sensor, the sensor string, and/or the sensor strip within the wound. The positioning device, for example, sensor tags and component 605, can include the light source or electromagnetic source that is used convey location, positioning, and orientation information to the imager or another detector as described herein.

The sensor tag, string, and strip can be positioned on a film or membrane similar to a wound contact layer as described with FIGS. 3A-3H. In some embodiments, the sensor tag, sting, and strip can be separate pieces of material provided and positioned separate from the wound contact layer of the dressing.

Figure 7:
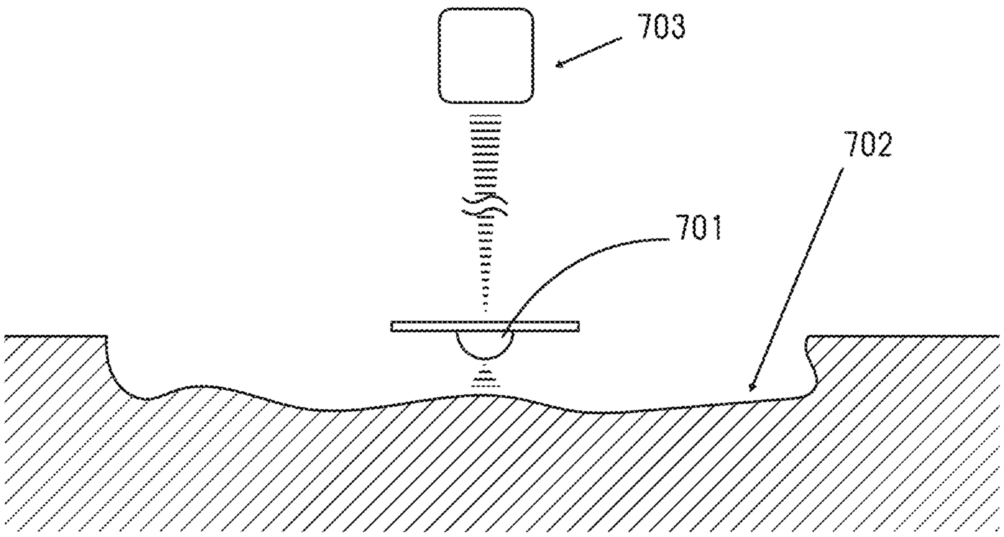
FIG. 7 illustrates a location detection system according to some embodiments.

FIG. 7 illustrates a location detection system according to some embodiment. In some embodiments, an LED or another electromagnetic (EM) source 701 can be positioned in the wound over the wound surface 702. The light from the LED can be communicated to an external device 703, for example, an imager, to be detected. For example, an LED sensor can shine bright light into the tissue, and the imager (e.g. camera) then detects the radiation through the tissue to image the wound. In some embodiments, the light or EM source does not need to emanate in the sensor layer (sensor tag, sensor strip, sensor string). The light or EM source can be a light-pipe, EM pipe, aerial, or resonator that allows transfer of EM to the wound surface.

In some embodiments, the imager can include a camera application on a smartphone. The imager can be placed or positioned in a vertical position over the wound area to image the wound and sensors positioned within and around the wound. The light sources can be triggered to pulse light in a sequence or with different wavelengths. The transmission of light from the light source can allow for identification of the location of the light source on and around the wound. The imager can then identify the fact that an LED (or other transmission source) is on through direct light from the sensor or through back-scatter from either the tissue or elements placed in front of the source intentionally. For example, in some embodiments, coatings (e.g. pH sensitive, polarizing, dissolvable, anti-microbial) can be applied on the wound-contact side of the dressing. When back-scatter is used, the image can be processed to identify the center of the light.

The imager or another detector can receive and collect the information of the location of the light source or other transmitted data. In some embodiments, the imager or another detector can be in communication with a controller, such using wireless communication. The controller can use the data obtained by the imager or another device to determine a position and/or orientation in the wound of a sensor, a sensor strip, and/or sensor string based at least on the received emplacement or positioning data and a relationship between positions and/or orientations in the wound dressing and/or the wound of the positioning device and the sensor, sensor strip, and/or sensor string. In some embodiments, the imager or another detector can receive information wirelessly from one or more light sources (LEDs) on or near the wound. In some embodiments, the light sources can be flashing in various colors or patterns to wirelessly communicate information to the imager or receiver.

In some embodiments, other EM generation sources can be used instead of LEDs. For example, radio or microwave pulses can be generated by one or more antennas, which may be driven by a common processor. A detector can detect the radio or microwave pulses. The detector can determine positioning or location of the source. As another example, small resistors powered to generate a localized rise in heat can be used. The heat can then be detected by a detector in the infrared spectrum (IR). The detector can determine positioning or location of the source. In some embodiments, the detector can be used to monitor how the temperature propagates through the tissue and thereby identifying the underlying blood flow and physiology. In some embodiments, the sensors can be thermal sensors. For example, a flashlight or torch on a smart phone or another device can be turned on, the flashlight or torch can get hot, and the rising temperature or heat can be detected by the thermal sensors and the sensors can communicate or indicate detection of heat. This can provide information on the location of the sensors. In some embodiments, the localized heating can be used for healing acceleration within the wound.

Figure 8:
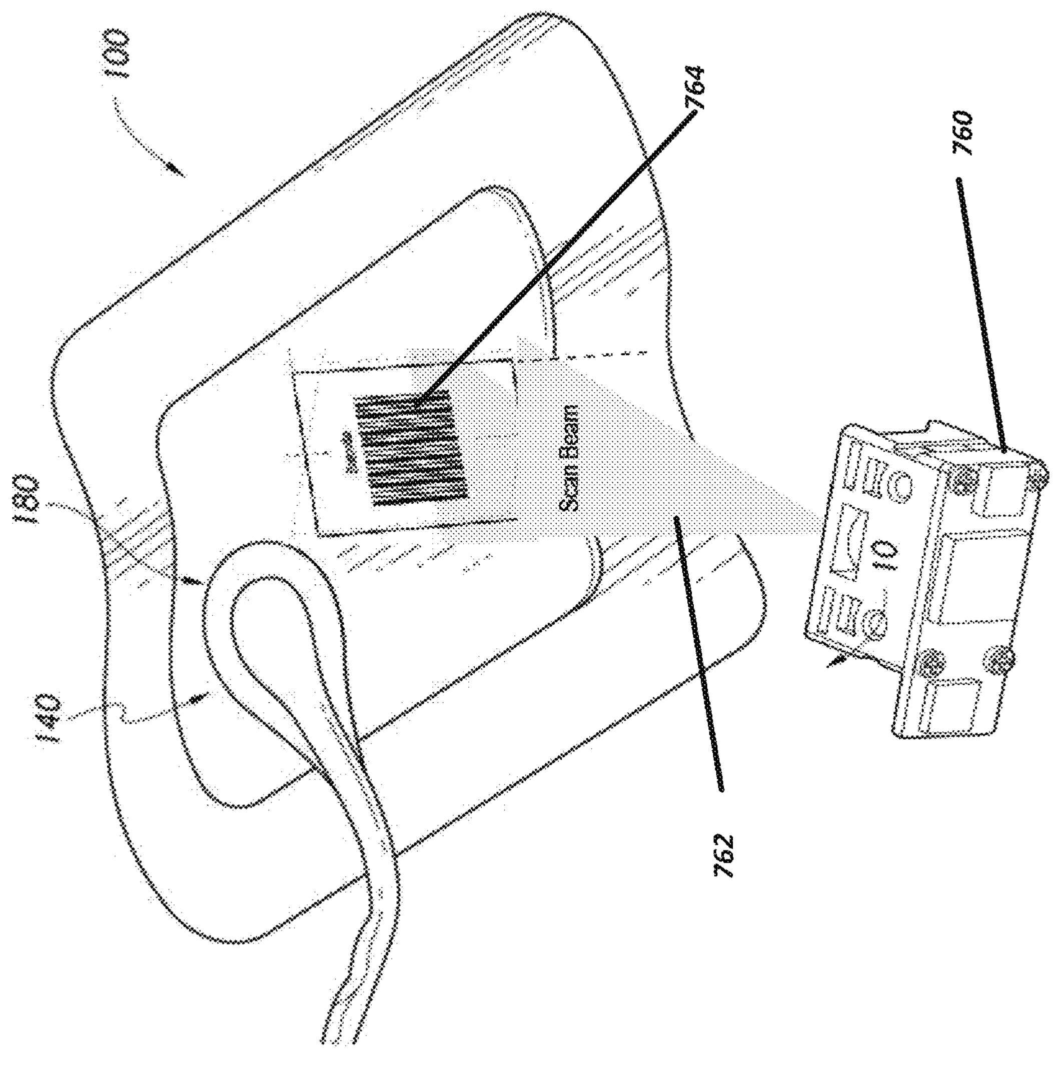
FIG. 8 illustrates a sensor tag scanned by an imager to provide information for sensor layout and positioning according to some embodiments.

In some embodiments, the sensor tags or positioning devices, such as those described with reference to FIGS. 6A, 6B, and/or 6D, can include a coded image or marking on a side of the tag facing away from the wound. In some embodiments, the coded image or marking can include a barcode, a number, a letter, an alphanumeric code, a standard shape, an irregular shape, and/or a logo. This coded image or marking can be identified by the imager to identify a location, orientation, and inclination of the coded image to the camera. In some embodiments, the image or marking can be a 2D barcode similar to the barcode 764 on mid-wound sensor tag or positioning device of FIG. 8. In some embodiments, the barcode 764 can include a 2D barcode or QR code. The barcode 764 can be scanned by the imager 760 at a range defined by the scan beam. In some embodiments, the relationship between the scan beam 762, imager 760 and barcode 764 can provide location, orientation, and inclination information that can be related to the sensor positioning and location.

In some embodiments, the print can be in a specific color for each location or grade along the sting or strip. In some embodiments, the tag, strip, or string can include a rainbow of colors printed continuously or in small portions along a strip. This would allow the imager to detect the location of a sensor by comparing that location to the known locations that match the correct color that is detected. In some embodiments, the color can be provided as a spot, shape, QR code of various colors, and/or a gradient of colors. In some embodiments, the sensor tag, strip, or string can be color coded to have a top and bottom surface to assist with orientation and alignment of the string. In some embodiments, a portion of or the whole of the tag, strip, or string can act as a marking or identifier. In some embodiments, a serial number or unique device identifier (UDI) or other code on the device could be used as an alpha numeric identifier.

In some embodiments, one or more sensors can be positioned at a particular location(s) on a substrate or layer. A marker, such as a color marker or other design, can be included to guide the user which way the one or more sensors or the sensor sheet, strip, string, or tag should be positioned in a wound. In some embodiments, the sensor sheet, strip, string, or tag can be sided and a marker can be used to allow the user to readily determine which direction to place the sensor system in the wound.

In some embodiments, the image to be captured by an imager can be visible to the human eye. In other embodiments, the image to be captured by the imager can be within the visible spectrum, but be invisible to the human eye. For example, the image can be in the ultraviolet spectrum (UV). In some embodiments, the image may fluoresce at one or more excitation spectra which can be triggered by a lamp on the imager.

Figure 9A:
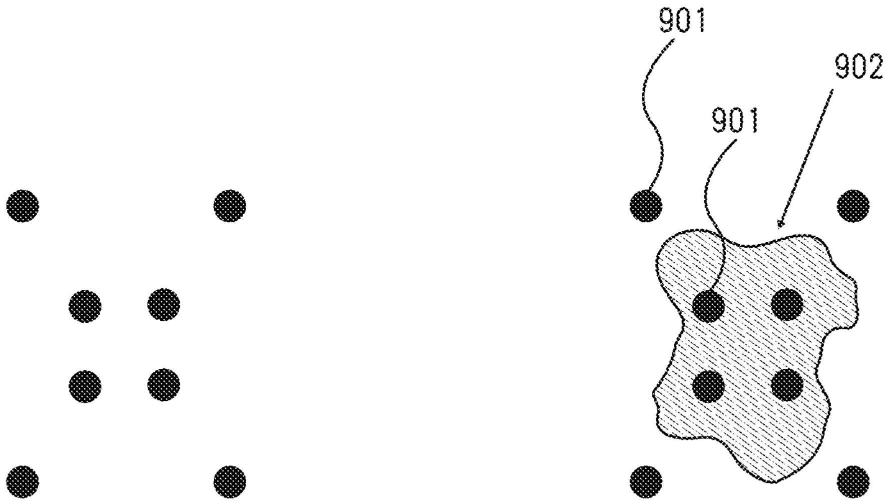
FIGS. 9A-9B illustrates the placement of positioning sensors in relation to a wound area according to some embodiments.
Figure 9B:
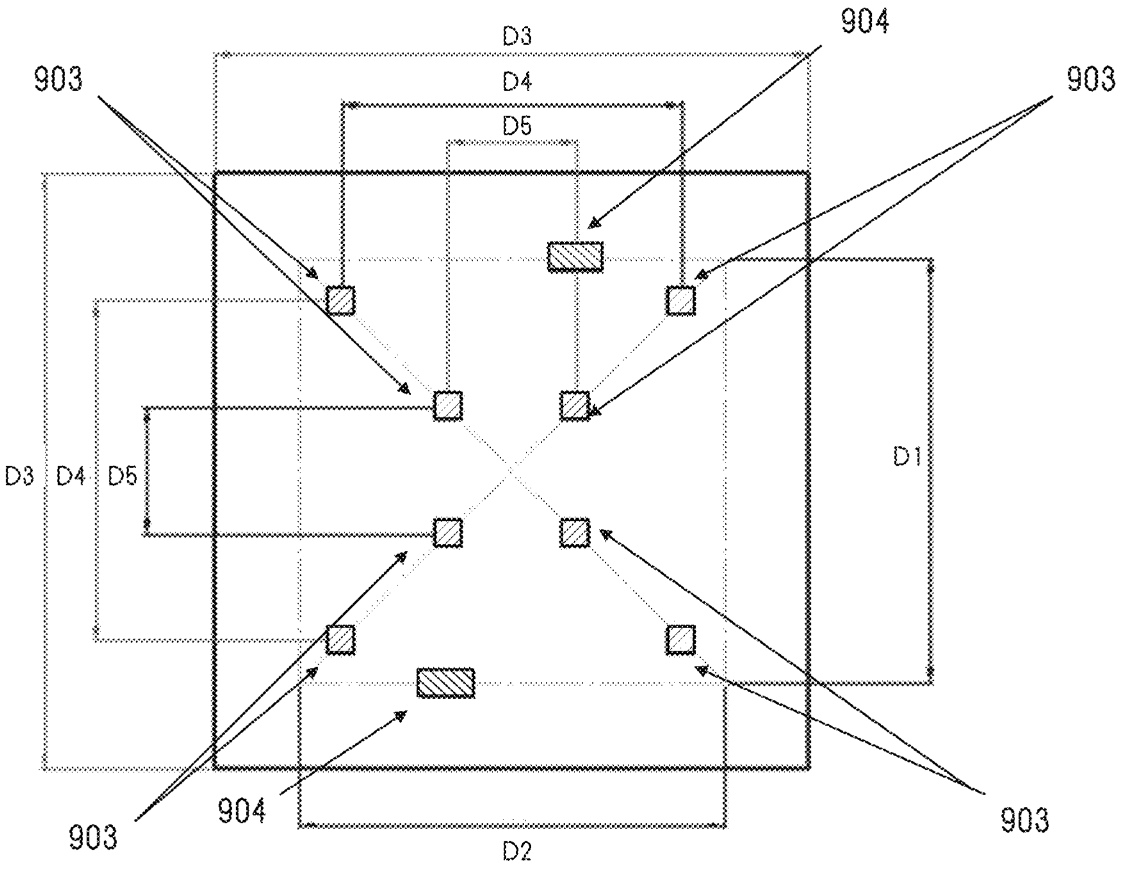

FIG. 9A illustrates the placement of positioning sensors in relation to a wound area defined by the wound edge 902. In some embodiments, the sensors 901 can be provided in the wound area or periwound area to collect data from the wound. FIG. 9B illustrates sensor positioning the can be used for impedance measurement. In some embodiments, the sensors can be positioned to have some measurement paths between sensors in the wound (positioned in the inner square), in the periwound (positioned in the outer square), and crossing the wound boundary. The set of eight measurement pads 903 of FIG. 9B illustrate a layout designed for impedance measurement. The drive circuit sensors 904 can also be arranged relative to the measurement pads 903.

Figure 10A:
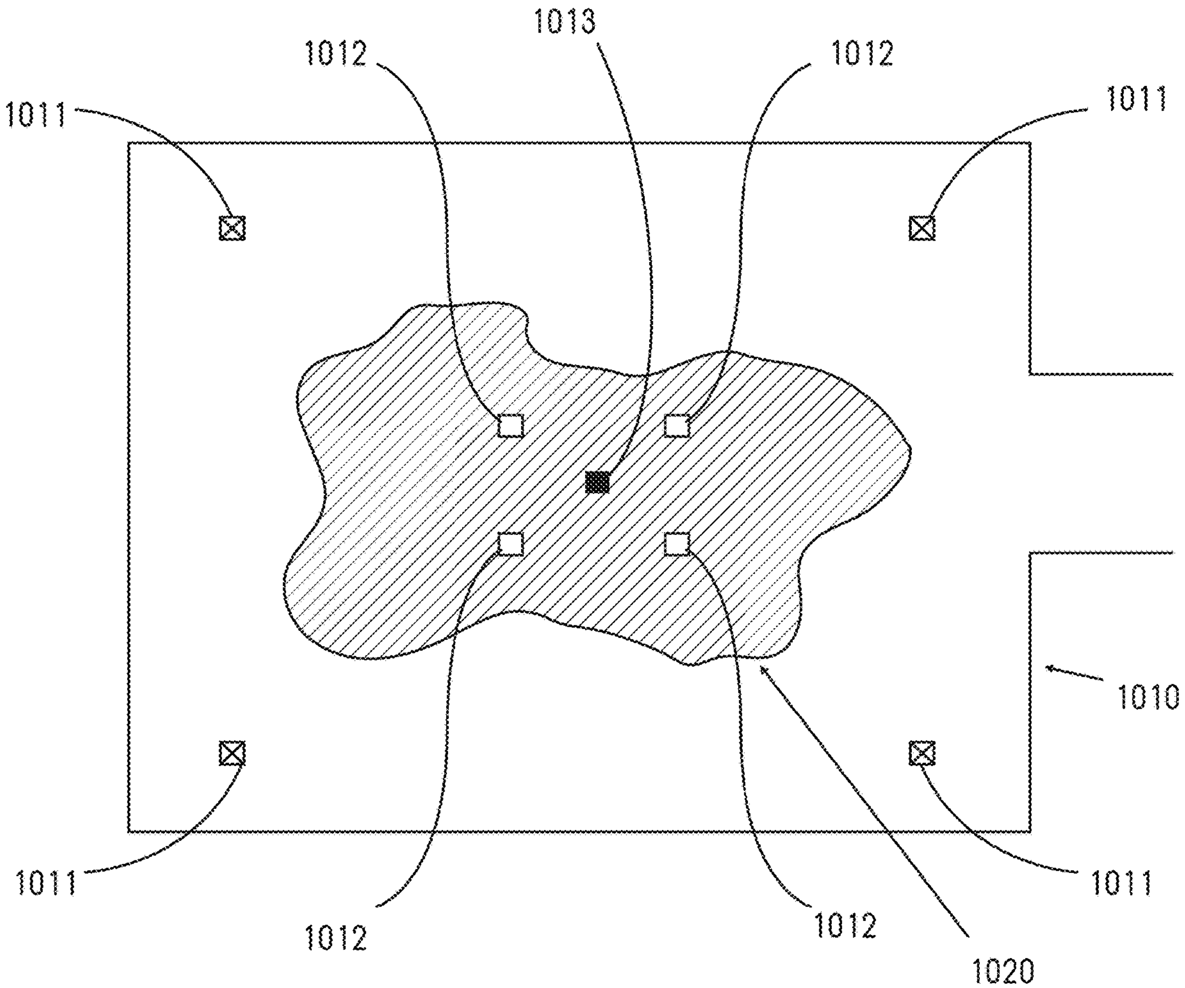
FIGS. 10A-10C illustrate an array of sensors positioned on or above the skin, wound edge, and wound center according to some embodiments.
Figure 10B:
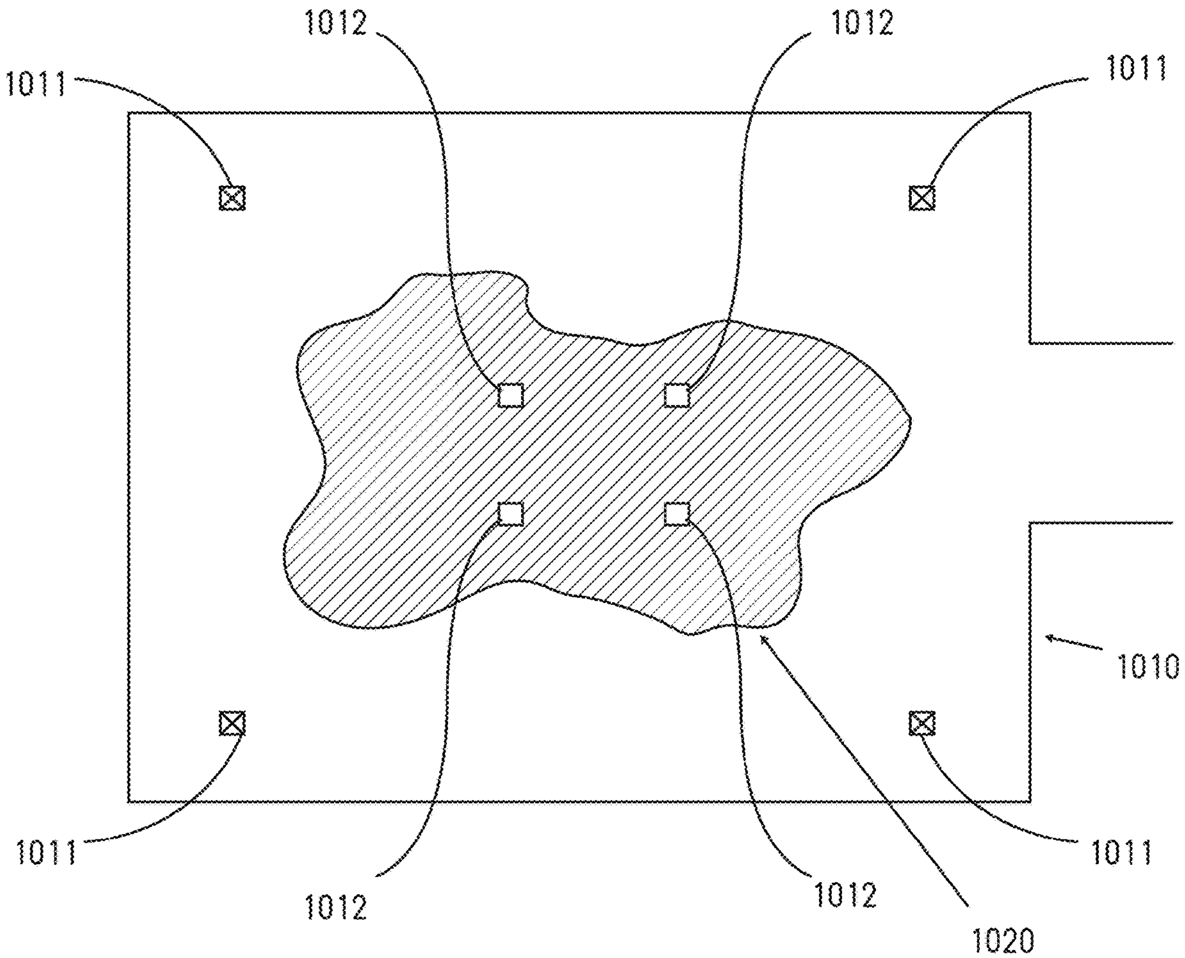
Figure 10C:
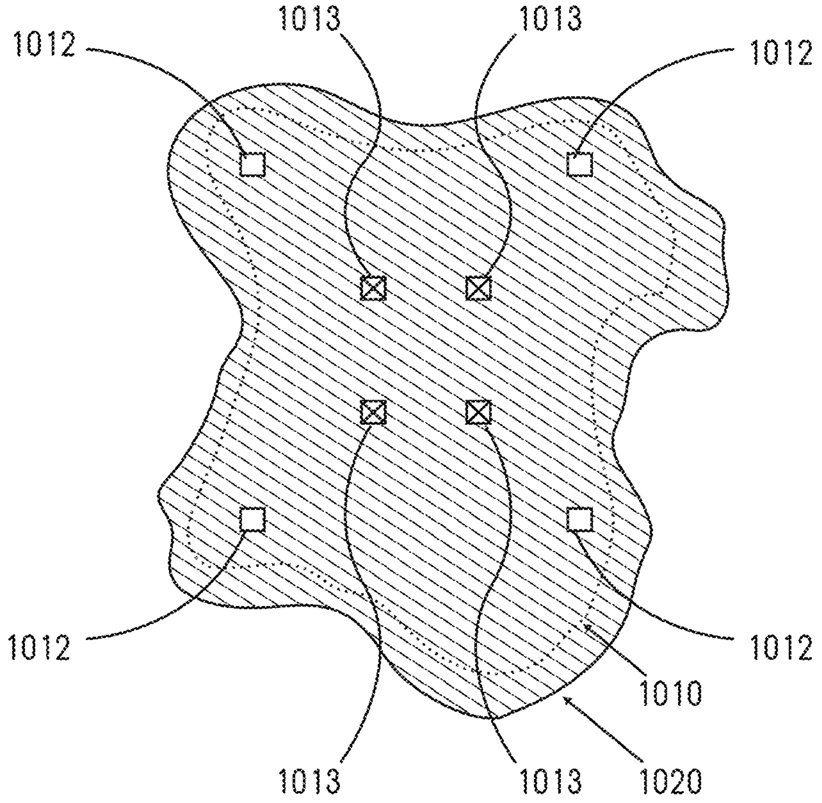

FIGS. 10A-10C illustrate an array of sensors positioned on or above the skin (or periwound area of the skin), wound edge, and wound center according to some embodiments. In some embodiments, the sensor array can be incorporated into a wound contact layer or sheet 1010 as described herein. The array can include periwound sensors 1011 that are positioned on the skin surrounding the wound 1020 or the periwound area as shown in FIGS. 10A and 10B. Wound edge sensors 1012 can also be included in the sensor array and can be positioned within the wound at or near the wound edge as shown in FIGS. 10A-10C. Wound center sensors 1013 can be provided in the wound at or near the wound center as shown in FIGS. 10A and 10C. FIG. 10C illustrates an embodiments of the wound contact layer 1010 with sensors 1012 and 1013 positioned in the wound 1020. In some embodiments, the wound contact layer 1010 could be cut, folded, scrunched, packed, or pre-shaped to fit into the wound. In some embodiments, one or more of the sensors or sensor arrays illustrated in and described with reference to FIGS. 10A-10C can be positioned on sensor sheets, sensor strings, sensor strips, and/or sensor tabs or tags as described herein.

Figure 11A:
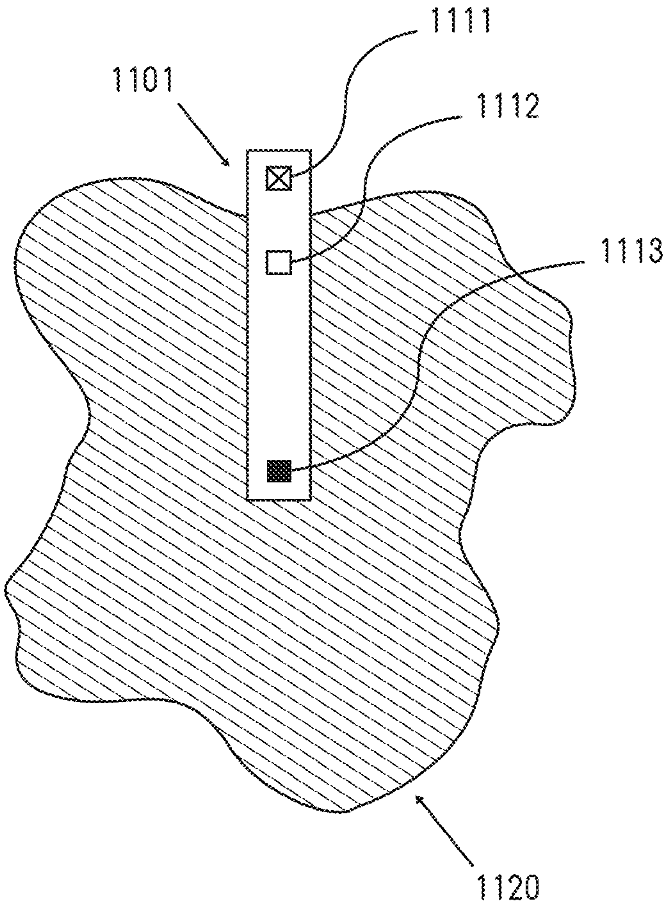
FIGS. 11A-11E illustrates some embodiments of sensors, sensor strips, and sensor tags positioned in and around a wound.
Figure 11B:
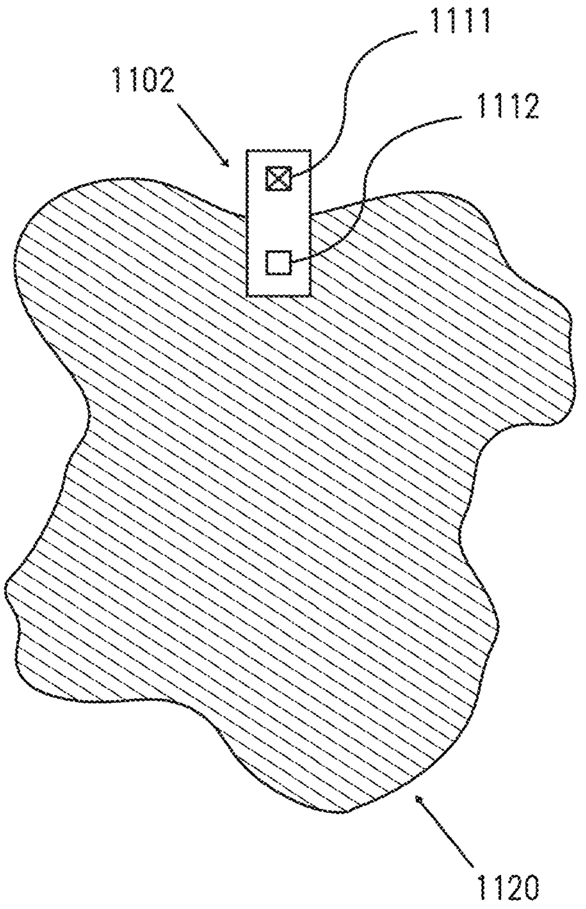

FIGS. 11A and 11B illustrate some embodiments of sensor strips and tags or tabs similar to the embodiments described with reference to FIGS. 6A and 6B positioned in and around a wound 1120. As shown in FIG. 11A, the sensor strip 1101 can include periwound sensors 1111 on the periwound skin, wound edge sensors 1112 positioned within the wound but on or near the wound edge, and wound center sensors 1113 positioned in the wound at or near the center of the wound. FIG. 11B illustrates a sensor tab 1102 spanning the wound edge. As used herein, sensor tags and sensor tabs refer to one or more sensors positioned on a small piece of material that can be used to sense wound characteristics and sensor tags and sensor tabs can be used interchangeable herein. The sensor tab or tag 1120 can include periwound sensors 1111 positioned on the periwound skin and wound edge sensors 1112 positioned in the wound on or near the wound edge. In some embodiments, the sensor tab or tag 1120 can be positioned at or near the center of the wound and can contain wound center sensors 1113 as described with reference to FIG. 6A.

Figure 11C:
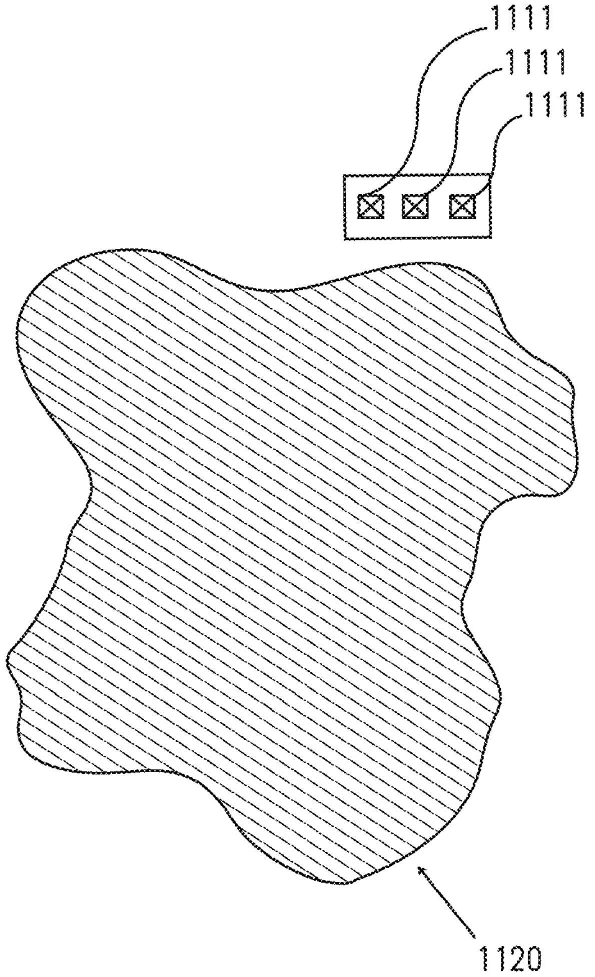
Figure 11D:
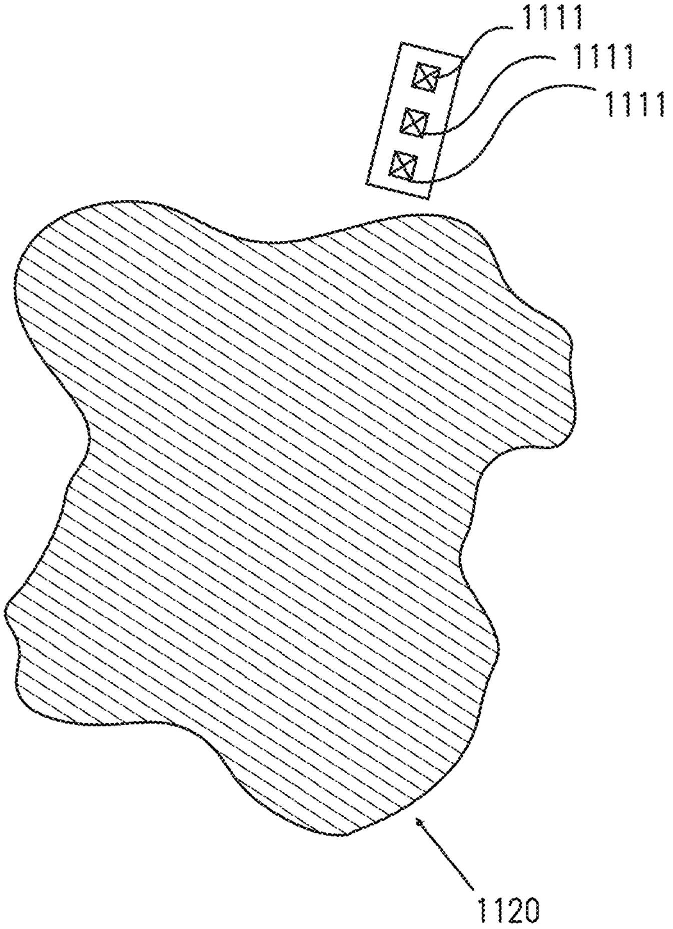

FIGS. 11C and 11D illustrate a sensor strip or sensor tag positioned external to or outside of the wound area according to some embodiments. FIG. 11C illustrates periwound sensors 1111 positioned outside the wound 1120 on the periwound skin or skin surrounding the wound. In some embodiments, the periwound sensors 1111 can be positioned outside the wound 1120 on the periwound skin or skin surrounding the wound parallel or substantially parallel to an edge of the wound 1120 as illustrated in FIG. 11C. FIG. 11D illustrates periwound sensors 1111 positioned in a proximal to distal arrangement relative to the wound.

Figure 11E:
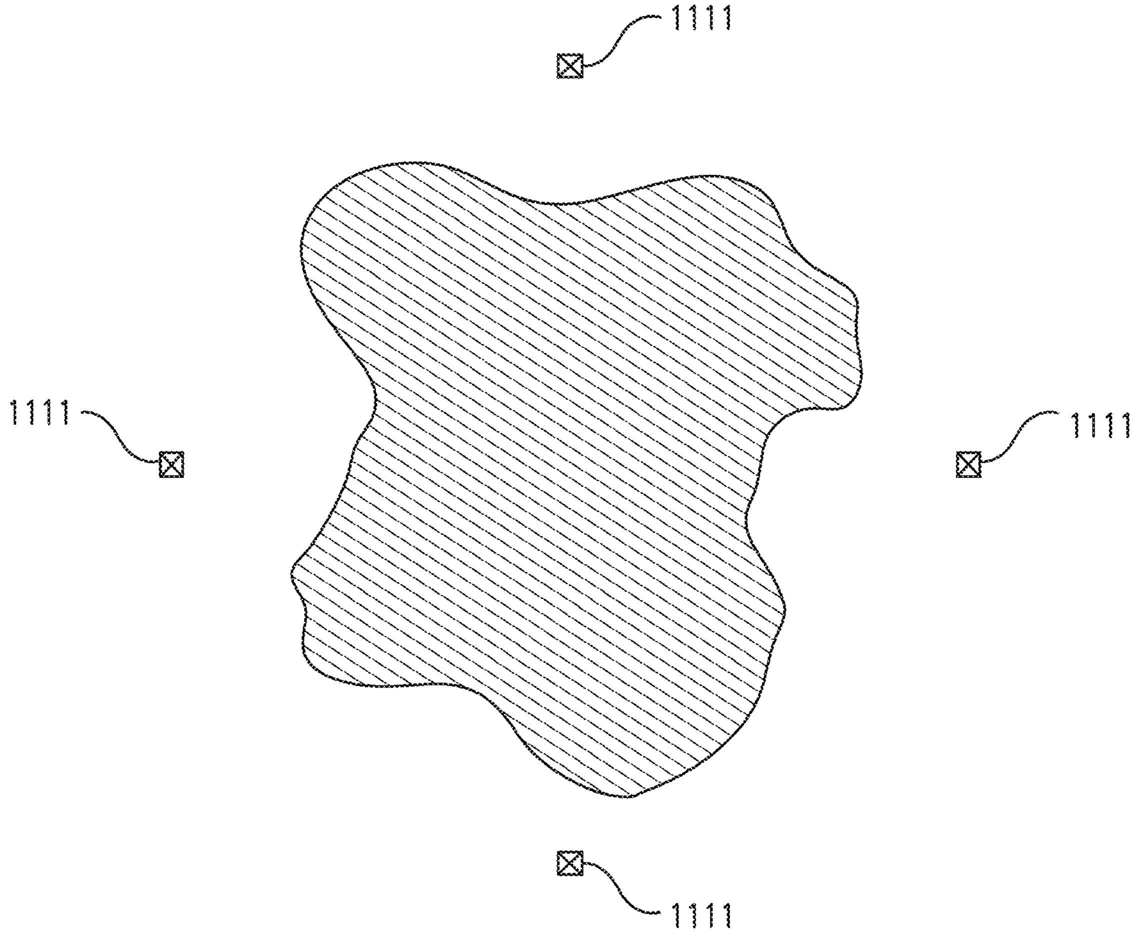

FIG. 11E illustrates sensors positioned at four positions or poles around the wound according to some embodiments. The four positions or poles of the wound 1120 can allow for measurement of physiologically relevant characteristics and markers, for example, perfusion. The sensors can be periwound sensors 1111 positioned on the periwound skin and located at specific points around the wound.

In some embodiments, sensors can be positioned in a drainage tube where the passage of wound exudate would be expected. In some embodiments, the drainage could be facilitated through aspiration or NPWT. In some embodiments, the sensors can be in the canisters distal to the tube. Sensors can be in dressings exposed to wound exudate, for example single use negative pressure wound therapy dressings (e.g. Smith & Nephew PICO), foam dressings (e.g. Smith & Nephew ALLEVYN), hydrogel or hydrofiber dressings (e.g. Smith & Nephew DURAFIBER).

Figure 12:
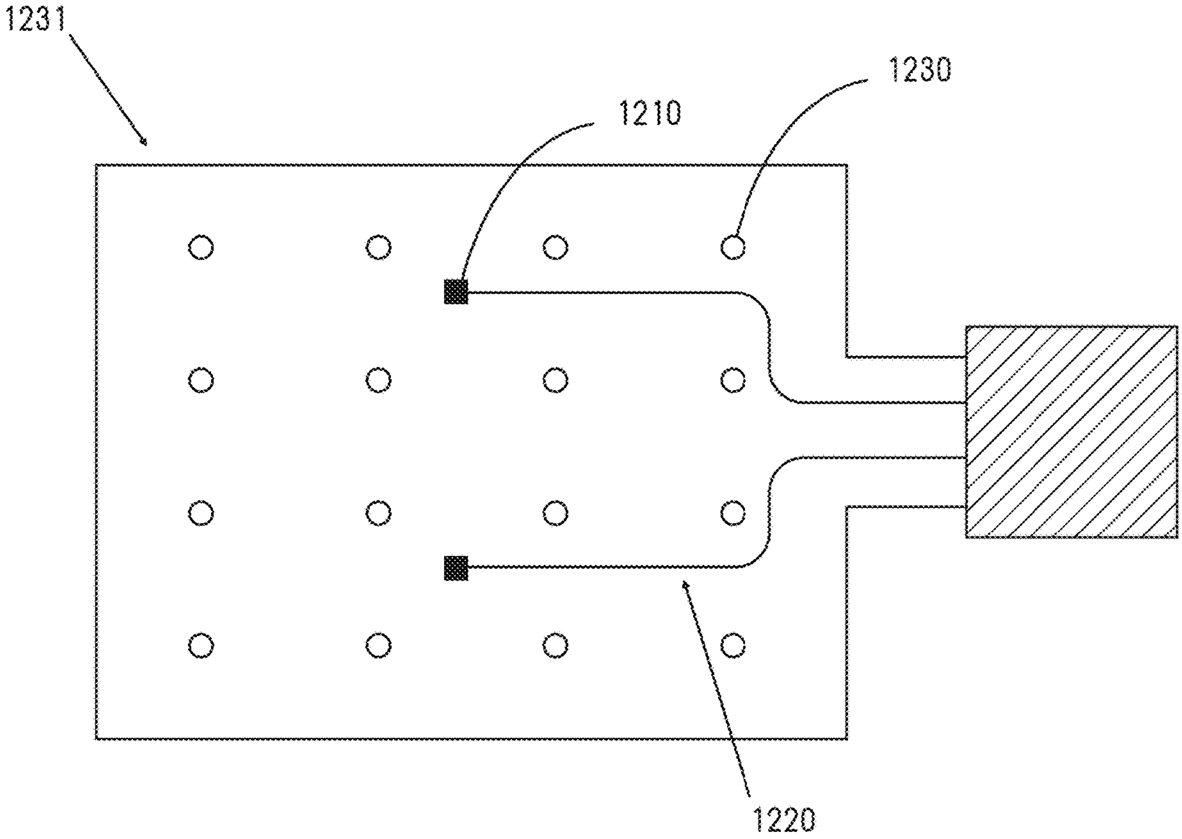
FIG. 12 illustrates sensors placed within the wound on tracks positioned around the perforations in the wound contact layer according to some embodiments.

FIG. 12 illustrates sensors 1210 placed within the wound on tracks 1220 that are positioned around the perforations 1230 in the wound contact layer 1231. In some embodiments, the tracks can be electrically conductive. The tracks can be sufficiently spaced apart to minimize effect of electrostatic discharge (ESD). In some embodiments, the tracks can be arranged to form a tail region. The tracks can come together at the tail region to allow a flexible tail to be generated, as disclosed herein. In some implementations, there may be a gap between the tracks forming the tail and/or between the tail and the tracks on the wound contact layer to minimize the ESD. In some embodiments, coatings or materials, such as ESD or anti-static coating or materials, can help mitigate effects of ESD.

Figure 13A:
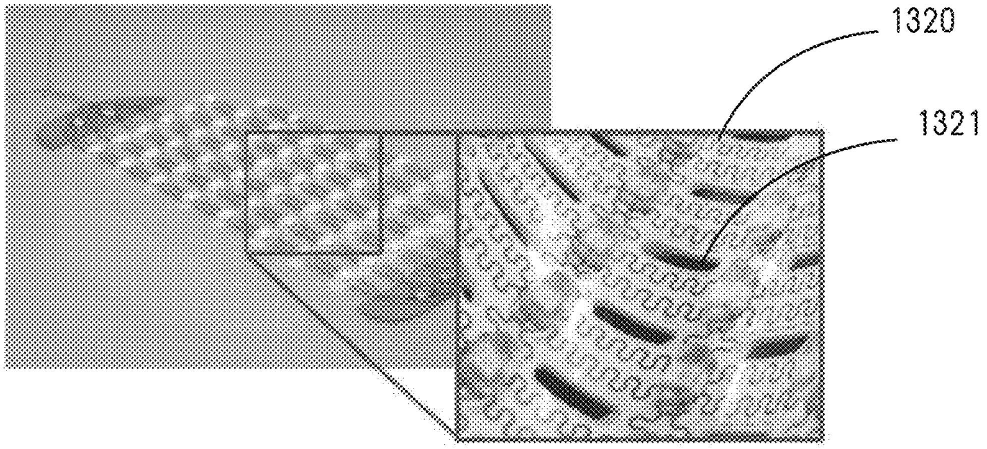
FIGS. 13A and 13B illustrates examples of track layouts for sensors to be used within a wound dressing.
Figure 13B:
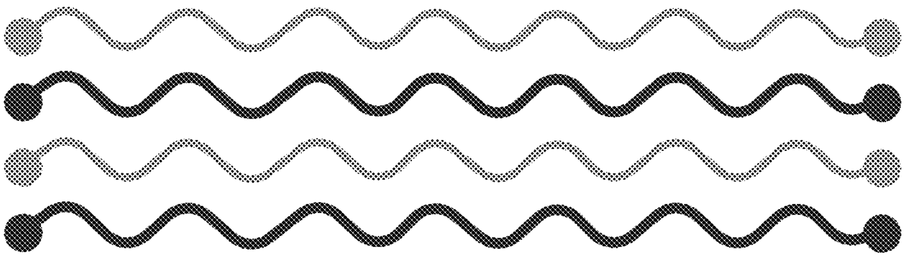

In some embodiments, the tracks with sensors described herein can be positioned in a layout that allows the material and tracks to be stretched, while retaining functionality. In some embodiments, the tracks can be laid out in a meandering or zig zag configuration to allow stretching, which may happen in use. FIGS. 13A and 13B illustrates examples of track layouts that can be used according to some embodiments.

FIG. 13A illustrates an example of a material with sensor tracks 1320 and perforations or slits 1321 in the material. It can be useful to provide perforations and slits in the material supporting the sensors and/or tracks to allow for fluid movement through the material as well as conformability and flexibility of the material.

Figure 14A:
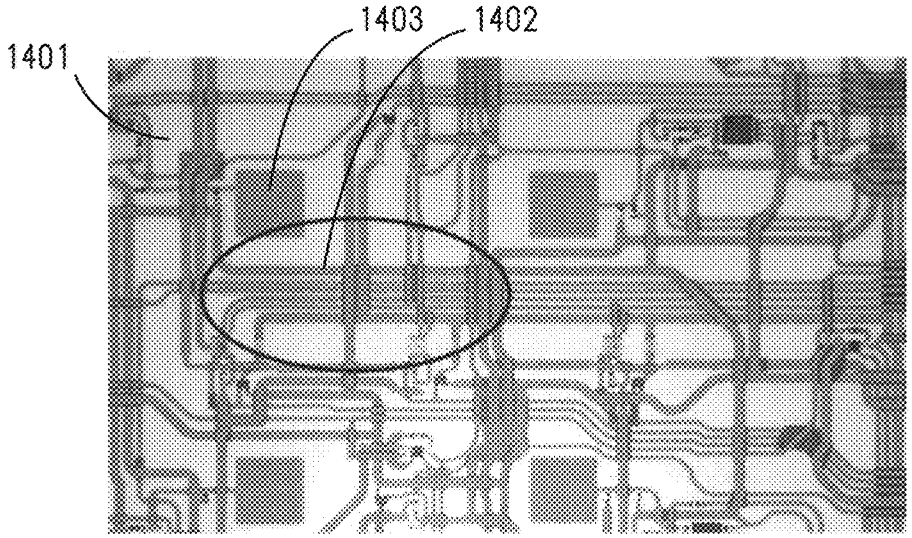
FIGS. 14A-14C illustrate embodiments of the sensor tracks and/or sensor arrays arranged on a support material.
Figure 14B:
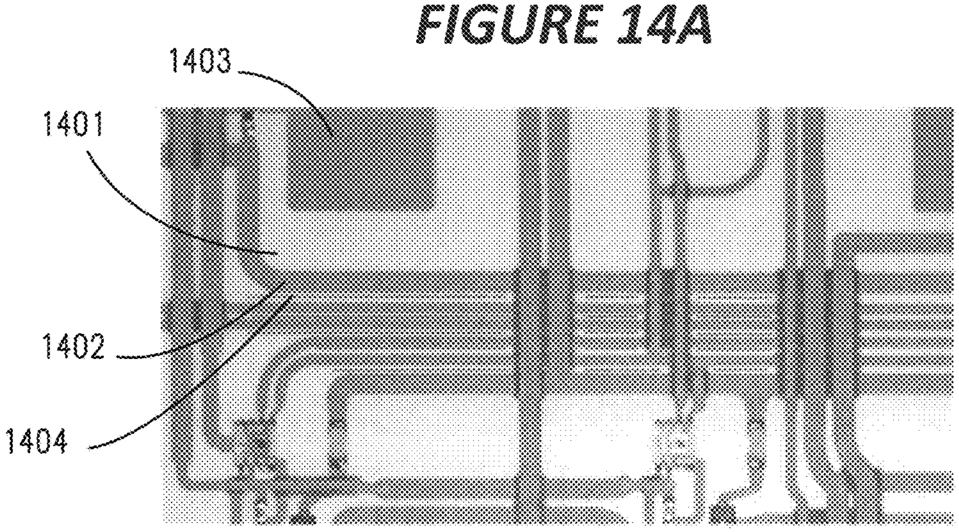
Figure 14C:
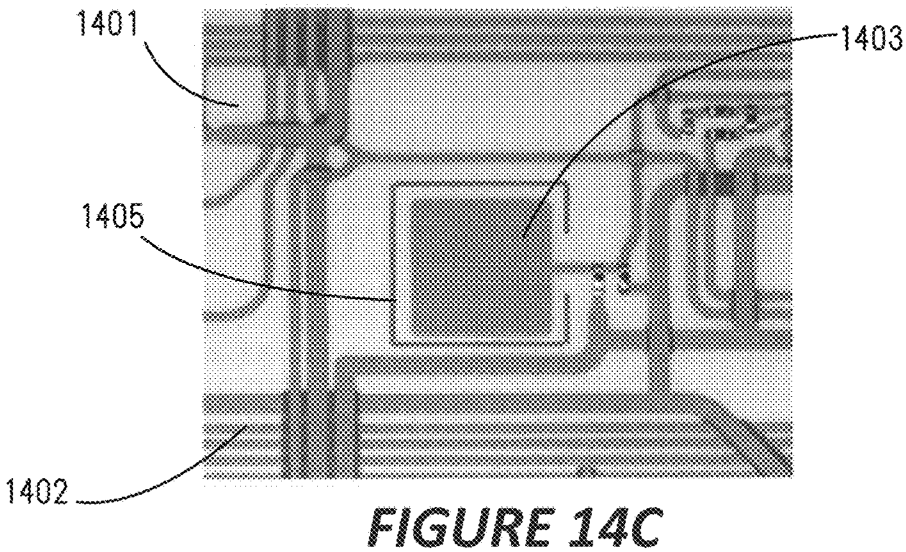

In some embodiments, the sensor sheet, sensor strip, sensor tag, sensor string, and/or other material supporting a sensor or sensor array as described herein can be perforated or cut to form slits. The perforations or slits can provide fluid movement through the material supporting the sensor or sensor array. FIGS. 14A-14C illustrate embodiments of the sensor tracks and/or sensor arrays arranged on a substrate or support material 1401. The fixed location of the tracks 1402 and components 1403 on the support material 1401 can lead to decreased breathability, extensibility, flexibility, and conformity. The support material 1401 can be perforated or slit in areas between the tracks 1402 or components 1403, such as to allow wound exudate to pass through the wound contact layer. In some embodiments, the perforation or slit can be created using a laser beam. The tracks 1402 can provide electrical connection between the components 1403, which can be one or more sensors or other electrical components as described herein.

The support material 1401 can be a wound contact layer. The wound contact layer can be flexible, elastic, or stretchable or substantially flexible, elastic, or stretchable in order to conform to or cover the wound. For example, the wound contact layer can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. Additional details of the support material 1401, tracks 1402, and components 1403 are described in International Patent Application No. PCT/EP2018/059333, filed Apr. 11, 2018, which is incorporated by reference in its entirety.

Any portion of the support material 1401 can be slit or perforated as necessary to facilitate or provide one or more of breathability, extensibility, flexibility, conformity, or fluid transfer or movement for the use of the device. For example, in some embodiments, the perforations or slits can be used in areas of dense track population on the support material to allow those areas to become breathable. The perforations or slits can also allow the dense areas of support material to conform more easily to areas in the wound. FIGS. 14A and 14B illustrate an embodiment of a support material 1401 with tracks 1402 that are separated by cuts or slits 1404 between the tracks. FIG. 14B is a zoomed in portion of the circled region in FIG. 14A. The slit 1404 is shown between the tracks 1402 as shown in FIG. 14B. Perforations or slits in the support material can cause physical separation of the tracks without damaging the circuitry.

FIG. 14C illustrates an embodiment of a support material 1401 with tracks 1402 and components 1403. The support material 1401 can have a slit 1405 cut substantially around the perimeter of the component 1403 as shown in FIG. 14C. The slit 1405 around the perimeter of the component 1403 can form a peninsular. In some embodiments, the slit 1405 around the perimeter of the component 1403 can allow the component 1403 to maintain contact with the wound while the rest of the support material 1401 undergoes stress, such as due to patient movement. For example, the component 1403 can comprise a conductive pad for measuring impedance and the slit 1405 around the perimeter of the conductive pad can allow the conductive pad to maintain contact with the wound while the rest of the support material undergoes stress within the wound and at least partially loses contact with the wound. In some embodiments, the slits can be provided on the support material in addition to or in place of the perforations 1230 of the material sheet 1231 described with reference to FIG. 12. In some embodiments, the support material 1401 can comprise a sensor sheet, sensor strip, sensor tag, sensor string, and/or other material supporting a sensor or sensor array and/or tracks as described herein. Additional details of stress on the one or more of support material 1401, tracks 1402, or components 1403 are described in International Patent Application No. PCT/EP2018/059333, filed Apr. 11, 2018, which is incorporated by reference in its entirety.

Terminology

Although some embodiments are described in connection with provision of negative pressure wound therapy, the disclosed systems and methods can be used in wound monitoring and/or treatment applications that do not apply negative pressure. Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A wound monitoring and/or therapy system, comprising:

a wound dressing configured to be positioned in contact with a wound, the wound dressing comprising:

an extensible material supporting a plurality of sensors on a linear sensor strip or string of sensors configured to measure one or more wound characteristics, wherein the plurality of sensors are configured to be positioned in at least one of the wound or an area surrounding the wound and the plurality of sensors are positioned on a wound-facing surface of the material so that the plurality of sensors comes into contact with the wound;

a positioning implement positioned in or on the wound dressing;

a detector configured to be positioned over the wound dressing when the wound dressing is positioned over the wound, wherein the detector is configured to collect positioning data from the positioning implement; and a controller configured to determine position and/or orientation in the wound of a first sensor from the plurality of sensors based on the positioning data.

2. The system of claim 1, wherein the material comprises a plurality of conductive tracks interconnecting the plurality of sensors and positioned on the material.

3. The system of claim 2, the plurality of conductive tracks are configured to maintain connectivity when the wound dressing has been stretched.

4. The system of claim 2, wherein the material comprises a plurality of slits positioned between at least two adjacent tracks, positioned between at least two adjacent sensors, or positioned between at least one track and at least one adjacent sensor.

5. The system of claim 1, wherein the plurality of sensors comprises at least one nanosensor, thermistor, conductivity sensor, Sp02 sensor, pH sensor, color sensor, optical sensor, impedance sensor, and/or electrode.

6. The system of claim 5, wherein the optical sensor comprises at least one of a red, green, blue, and clear (RGBC) sensor and/or red, green, blue, and white (RGBW) sensor.

7. The system of claim 1, wherein the positioning implement is configured to wirelessly communicate with the linear sensor strip or string of sensors.

8. The system of claim 1, wherein the positioning implement is configured to electrically communicate with the linear sensor strip or string of sensors.

9. The system of claim 1, wherein the detector is configured to determine the position and/or orientation in the wound of the first sensor of the plurality of sensors based at least on the indicated position and/or orientation and a relationship between positions and/or orientations in the wound dressing and/or the wound of the positioning implement and first sensor.

10. The system of claim 9, wherein the relationship comprises at least known position and/or orientation offset between the positioning implement and the first sensor.

11. The system of claim 1, wherein a portion of the positioning implement is configured to be positioned outside of the wound.

12. The system of claim 1, wherein the positioning implement comprises at least one marking configured to communicate positioning information.

13. The system of claim 12, wherein the at least one marking comprises at least one of a barcode, a number, a letter, an alphanumeric code, a standard shape, an irregular shape, or a logo.

14. The system of claim 1, wherein the wound dressing is configured to communicate negative pressure to the wound.

* * * * *